(12) United States Patent
McCreery

(10) Patent No.: US 8,249,723 B2
(45) Date of Patent: Aug. 21, 2012

(54) APPARATUS AND METHOD FOR TREATING OBSTRUCTIVE SLEEP APNEA

(75) Inventor: Douglas B. McCreery, Pasadena, CA (US)

(73) Assignee: Huntington Medical Research Institutes, Pasadena, CA (US)

(*) Notice: Subject to any disclaimer, the term of this patent is extended or adjusted under 35 U.S.C. 154(b) by 359 days.

(21) Appl. No.: 12/441,793

(22) PCT Filed: Sep. 27, 2007

(86) PCT No.: PCT/US2007/079717
§ 371 (c)(1),
(2), (4) Date: Mar. 18, 2009

(87) PCT Pub. No.: WO2008/039921
PCT Pub. Date: Apr. 3, 2008

(65) Prior Publication Data
US 2010/0087896 A1    Apr. 8, 2010

Related U.S. Application Data

(60) Provisional application No. 60/827,193, filed on Sep. 27, 2006.

(51) Int. Cl.
*A61N 1/32* (2006.01)
(52) U.S. Cl. ..................................... 607/134
(58) Field of Classification Search ............... 607/134; 600/534
See application file for complete search history.

(56) References Cited

U.S. PATENT DOCUMENTS

| 4,593,686 A | 6/1986 | Lloyd et al. |
| 5,792,067 A * | 8/1998 | Karell ........................... 600/534 |
| 6,598,006 B1 | 7/2003 | Honda et al. |
| 7,711,438 B2 * | 5/2010 | Lattner et al. ................. 607/134 |
| 7,890,193 B2 * | 2/2011 | Tingey .......................... 607/134 |
| 2003/0025082 A1 * | 2/2003 | Brewington et al. ...... 250/341.8 |
| 2007/0173893 A1 * | 7/2007 | Pitts ................................ 607/2 |

FOREIGN PATENT DOCUMENTS

| TW | 200501437 A | 1/2005 |
| WO | 9215364 A | 9/1992 |
| WO | 9718854 A | 5/1997 |

OTHER PUBLICATIONS

Fletcher, et al. "Glossometric measurements in vowel production and modification," Clinical Linguistics & Phonetics, 1989, vol. 3, No. 4; pp. 359-375.
Wrench, et al. "Optopalatograph (OPG): A new apparatus for speech production analysis," Proc. Intl. Conf. Spoken Language Processing, 1996; pp. 1589-1592.
English Abstract of TW 200501437, obtained from http://twpat6.tipo.gov.tw/tipotwoc/ on Mar. 22, 2012, 2 pages,
Extended European Search Report dated Sep. 23, 2009, received in European Application 07843352,1 filed Sep. 27, 2007, 9 pages.
International Search Report dated Apr. 18, 2008, received in PCT Application Pot/Usn/079717 filed on Sep. 27, 2007, 2 pages.

* cited by examiner

*Primary Examiner* — Scott Getzow
*Assistant Examiner* — Amanda Patton
(74) *Attorney, Agent, or Firm* — Heather M. Colburn; Davis Wright Tremaine LLP

(57) ABSTRACT

The present invention describes an apparatus, a system and a method for the treatment of obstructive sleep apnea. The treatment involves monitoring the position of the tongue and/or the force exerted by the tongue and electrical stimulation of the hypoglossal nerve to move the tongue into an anterior position or to maintain the tongue in an anterior position.

6 Claims, 17 Drawing Sheets

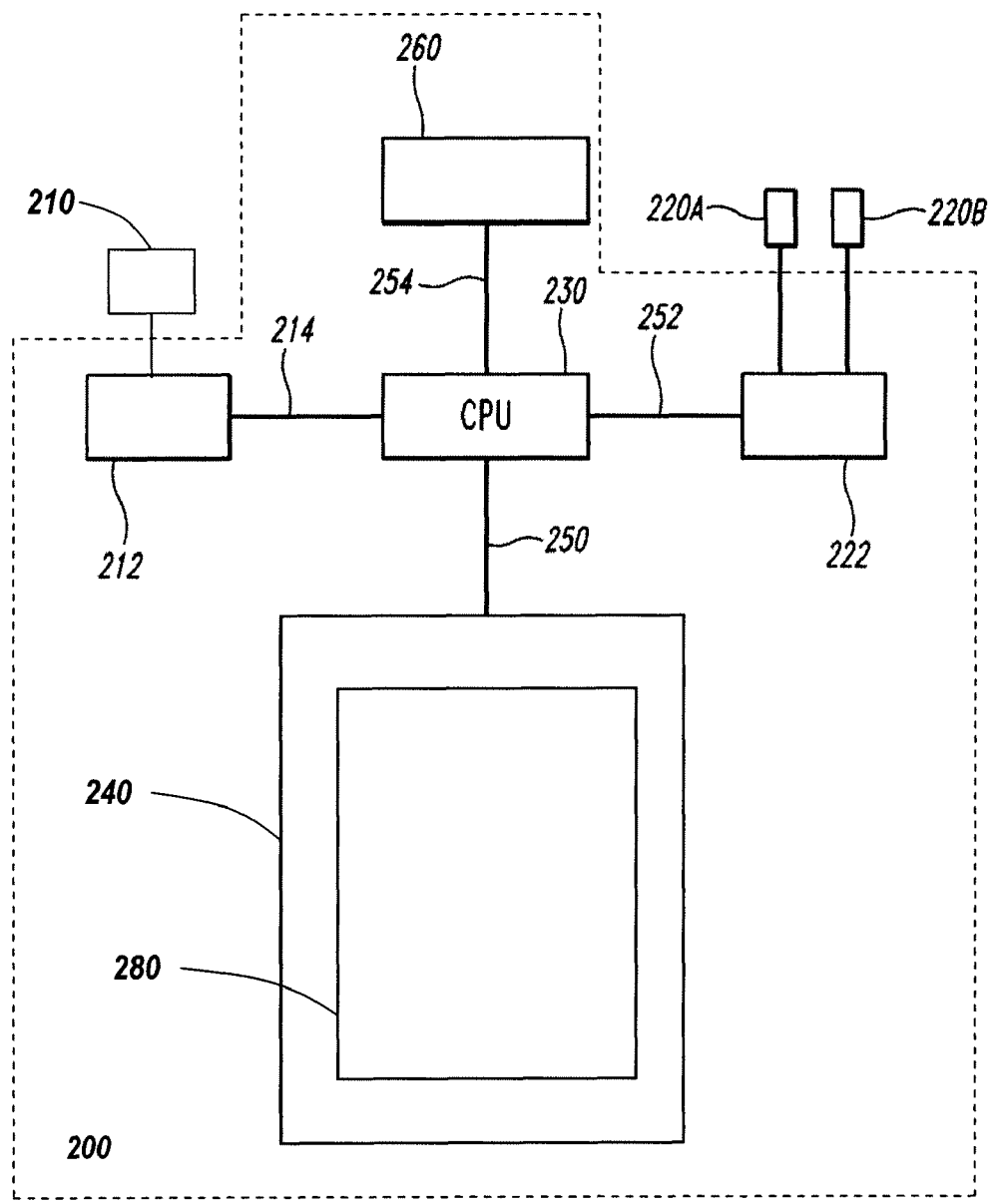

FIG. 5
A
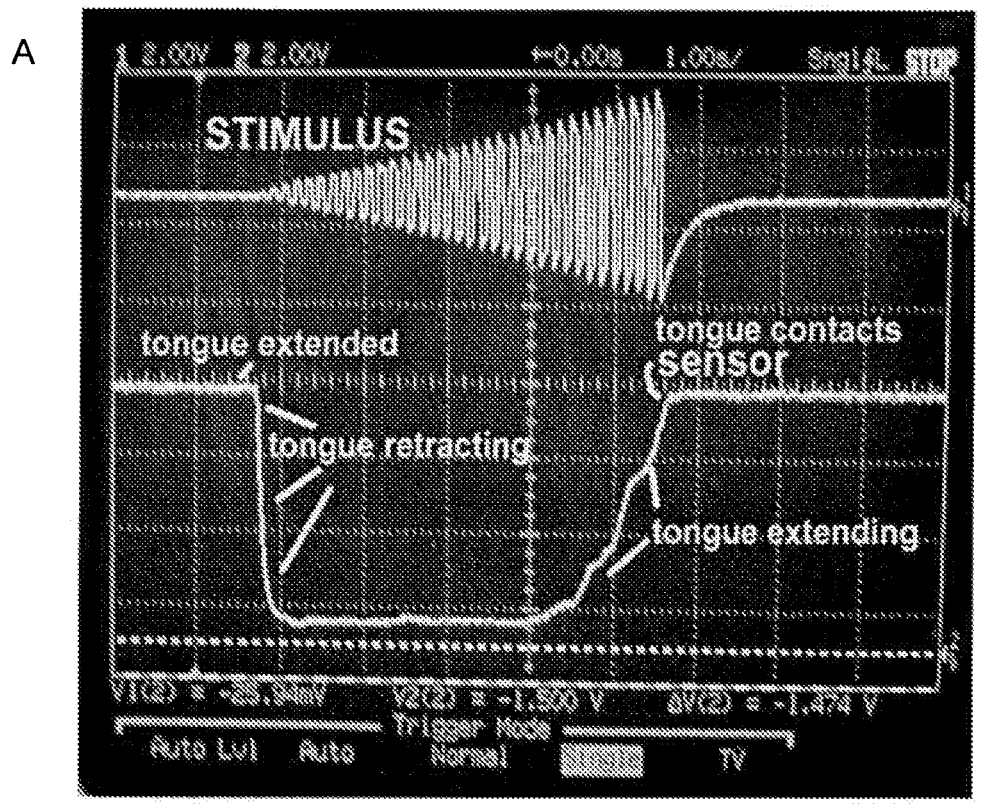
B
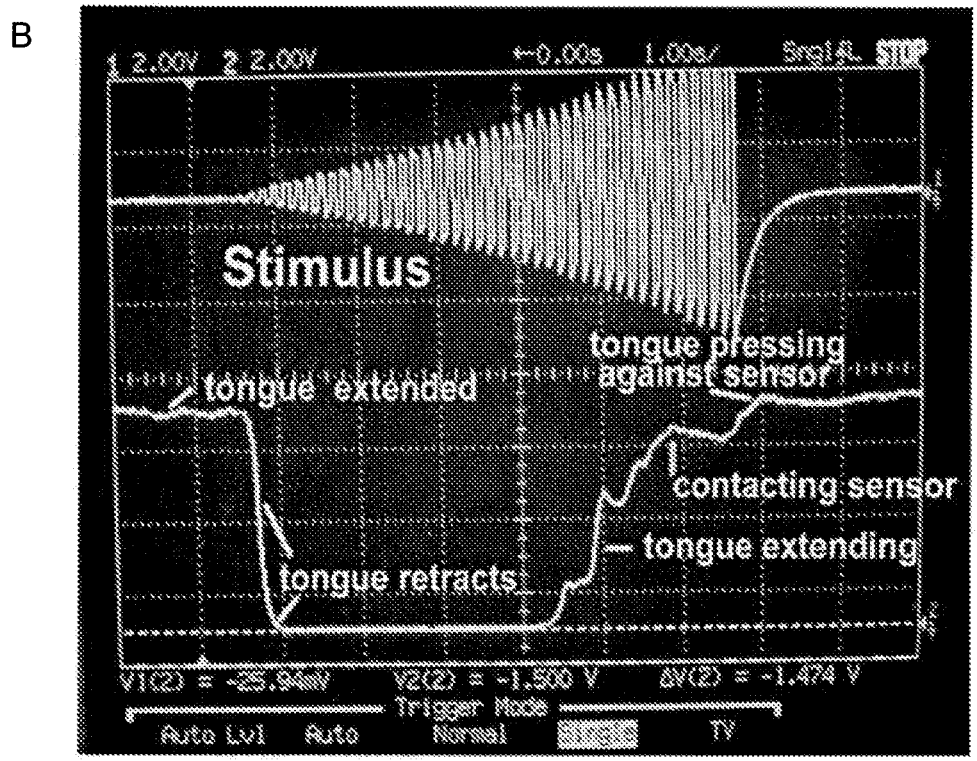

APPARATUS AND METHOD FOR TREATING OBSTRUCTIVE SLEEP APNEA

This application is the National Phase of International Application PCT/US07/79717, filed Sep. 27, 2007, which designated the U.S. and that International Application was published under PCT Article 21(2) in English. This application also includes a claim of priority under 35 U.S.C. §119(e) to U.S. provisional patent application No. 60/827,193, filed Sep. 27, 2006.

FIELD OF INVENTION

This invention relates to the use of electrical stimulation to treat obstructive sleep apnea.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Obstructive sleep apnea (OSA) is a prevalent disorder characterized by recurrent apneas during sleep, despite persisting respiratory effort. The cessation of respiration is due to obstruction of the upper airway, and induces hypoxia and hypercapnia, accompanied by cardiac arrhythmias and elevations of systemic and pulmonary arterial blood pressure (Mansfield et al., "Obstructive sleep apnoea, congestive heart failure and cardiovascular disease," *Heart Lung Circ*, vol. 14 Suppl 2, pp. S2-7, 2005; Peters, "Obstructive sleep apnea and cardiovascular disease," *Chest*, vol. 127, pp. 1-3, 2005; O'Donnell et al., "Airway obstruction during sleep increases blood pressure without arousal," *J Appl Physiol*, vol. 80, pp. 773-81, 1996; O'Donnell et al., "The effect of upper airway obstruction and arousal on peripheral arterial tonometry in obstructive sleep apnea," *Am J Respir Crit Care Med*, vol. 166, pp. 965-71, 2002). OSA is a strong risk factor for stroke, hypertension, atherosclerosis, cardiovascular disease, and increased postoperative morbidity after general anesthesia (Yaggi et al., "Obstructive sleep apnea as a risk factor for stroke and death," *N Engl J Med*, vol. 353, pp. 2034-41, 2005; He et al., "Mortality and apnea index in obstructive sleep apnea. Experience in 385 male patients," *Chest*, vol. 94, pp. 9-14, 1988). The frequent partial arousals throughout the night result in sleep deprivation and daytime tiredness and malaise.

Sleep-disordered breathing affects up to 9% of working-aged women and 24% of men (Peters, "Obstructive sleep apnea and cardiovascular disease," *Chest*, vol. 127, pp. 1-3, 2005). Total collapse of the airway with complete obstruction lasting 10 second or more and with a decrease in arterial oxyhemoglobin saturation of 4% or more is classified as OSA. Partial airway obstruction sufficient to cause a decrease in oxyhemoglobin saturation of 4% or more is designated as obstructive hypopnea. The severity of OSA usually is quantified by an apnea-hypoxia index (AHI), the number of apneic and hypoxic episodes per hour of sleep. The nearly universal use of the AHI recorded during polysomnography to characterize OSA has been criticized as being at best a surrogate for the cardiovascular effect of the disorder. For example, an AHI of 15 consisting exclusively of hypopneas and minor oxyhemoglobin desaturation (about 4-5% from baseline) would be of much less cardiovascular significance than the same AHI accompanied by severe hypoxia and hypercapnia. Thus repeated, transient oxyhemoglobin desaturation to 93% or less markedly increases mean arterial blood pressure (O'Donnell et al., "Airway obstruction during sleep increases blood pressure without arousal," *J Appl Physiol*, vol. 80, pp. 773-81, 1996). While criteria for clinical staging of OSA appear not to be well standardized, an AHI of about 5 to about 27 is generally considered mild-to-moderate OSA. This reflects the assumption that "normal" individuals may experience up to 5 episodes of hypopnea or apnea per hour with oxyhemoglobin desaturation of 4% or greater, and also the consensus that more than 5 such episodes per hour are associated with at least some increased risk of cardiovascular disease (Meoli et al., "Hypopnea in sleep-disordered breathing in adults," *Sleep*, vol. 24, pp. 469-70, 2001). Persons with severe OSA may experience 30 or more episodes per hour. Persons with an AHI of 20 or greater have markedly increased mortality relative to the general population (He et al., "Mortality and apnea index in obstructive sleep apnea. Experience in 385 male patients," *Chest*, vol. 94, pp. 9-14, 1988). Moderate-to-severe OSA is estimated to occur in at least 1-4% of working-aged adults in the generation population, with about a 2:1 preference for males, but a significant number of affected persons remain undiagnosed, so the prevalence may be considerably greater (Stierer et al., "Demographics and diagnosis of obstructive sleep apnea," *Anesthesiol Clin North America*, vol. 23, pp. 405-20, v, 2005).

A cardinal feature of OSA is the tendency for the soft tissues of the upper airway, specifically those of the velo- and oropharynx, to collapse during sleep, and thus occlude the airway. In healthy persons during sleep, the critical pressure for airway collapse ($P_{crit}$) ranges from about 0 to about −14 cm $H_2O$ so that a small partial vacuum within the airway is required in order to induce collapse (King et al., "A model of obstructive sleep apnea in normal humans. Role of the upper airway," *Am J Respir Crit Care Med*, vol. 161, pp. 1979-84, 2000). However, "healthy" persons in which $P_{crit}$ during sleep is close to 0 cm $H_2O$ tend to snore. For persons with OSA, as in healthy persons, the background tone in the muscles of the upper airway, and also phasic activity in the hypoglossal nerve associated with airway protective reflexes, maintain a negative $P_{crit}$ during wakefulness. However, during sleep, and especially during REM sleep, the reduction in the activity in the hypoglossal nerve results in a reduction in the tone and stiffness in the muscles of the upper airway, causing $P_{crit}$ to rise to or above atmospheric pressure, rendering the upper airway vulnerable to collapse. (Smith et al., "Upper airway pressure-flow relationships in obstructive sleep apnea," *J Appl Physiol*, vol. 64, pp. 789-95, 1988). The physiological and anatomical factors responsible for the elevated $P_{crit}$ in persons with OSA are complex and vary between patients, suggesting the need for treatment options that can be tailored to each patient's needs (Ryan et al., "Pathogenesis of obstructive sleep apnea," *J Appl Physiol*, vol. 99, pp. 2440-50, 2005).

A reduction in the tone of the muscles of the tongue base during sleep is an important contributor to the elevated $P_{crit}$ in persons with OSA. Also, in response to the decreased tone in the tongue extensor muscles, particularly the geneoglossus muscle, the tongue tends to prolapse onto the back of the pharynx, partially obstructing the airway (Feldman et al., "Slip of the tongue," *Am J Respir Crit Care Med*, vol. 170, pp. 581-2, 2004).

Continuous positive airway pressure by a nasal mask (nasal CPAP) relieves OSA by maintaining the airway at a positive pressure, slightly above $P_{crit}$ (Smith et al., "Upper airway pressure-flow relationships in obstructive sleep apnea," *J Appl Physiol*, vol. 64, pp. 789-95, 1988). There remains some controversy as to whether the effect is purely a passive inflation of the airway ("pneumatic splinting") or if the positive pressure also triggers protective airway reflexes (Goh et al., "Upper airway dilating forces during wakefulness and sleep in dogs," *J Appl Physiol*, vol. 61, pp. 2148-55, 1986). CPAP is very effective and currently is the gold standard for non-surgical treatment of moderate-to-severe OSA. However, the firm-fitting nasal mask and the associated hose line are often uncomfortable and encumbering, the sensation of continuous positive airway pressure is uncomfortable and disconcerting to many users and the device is generally regarded as a necessary evil, even by well-acclimated users. It has been reported that 8-15% of OSA patients refuse further use of CPAP after the first night (Krieger, "Therapeutic use of auto-CPAP," *Sleep Med Rev*, vol. 3, pp. 159-74, 1999). While CPAP technology has improved and protocols for achieving primary acceptance by patients also have been evolving in recent years, even "regular users" often employ their CPAP during only part of the night (e.g., 3.5-5 hours) and tend not to use it every night (Valenca et al., "[Compliance to positive airway pressure treatment in obstructive sleep apnea syndrome (OSAS).]," *Rev Port Pneumol*, vol. 11, pp. 52-3, 2005; Orth et al., "[Long-term compliance of cpap-therapy—update, predictors and interventions]," *Pneumologie*, vol. 60, pp. 480-4, 2006; Sin et al., "Long-term compliance rates to continuous positive airway pressure in obstructive sleep apnea: a population-based study," *Chest*, vol. 121, pp. 430-5, 2002). These persons are likely to remain at somewhat elevated risk for the cardiovascular complications of OSA, even if their compliance is adequate to allow sufficient restorative sleep to markedly improve the quality of day-to-day life. Clearly there is a need for effective alternatives to CPAP that will find better initial acceptance and long-term compliance. Such alternatives could be of considerable significance to public health if they also achieve greater initial acceptance and compliance by persons with moderate OSA, since this may prevent or delay progression to more severe stages. There is evidence that the chronic intermittent hypoxias of OSA lead to a conversion of the pharyngeal muscle fibers, which further increase collapsibility. Animal studies have demonstrated that after 10 hours of intermittent hypoxia, the geneoglossus muscle undergoes a conversion to myosin chain type 2A to 2B, which are much more fatigable (Pae et al., "Geniohyoid muscle properties and myosin heavy chain composition are altered after short-term intermittent hypoxic exposure," *J Appl Physiol*, vol. 98, pp. 889-94, 2005). Thus, In addition to the effects of sleep depravation on the respirator drive and the activity of the pharyngeal muscles, and compromise of protective airway reflexes by the reduced mechanical sensitivity of the pharyngeal mucosa, the intermittent hypoxia also promotes increased collapsibility of the upper airway (O'Halloren et al., "Chronic intermittent asphyxia impairs rat upper airway muscle responses to acute hypoxia and asphyxia," *Chest*, vol. 122, pp. 269-75, 2002; Bradford et al., "Does episodic hypoxia affect upper airway dilator muscle function? Implications for the pathophysiology of obstructive sleep apnoea," *Respir Physiol Neurobiol*, vol. 147, pp. 223-34, 2005).

Electrical stimulation of the hypoglossal nerve or of its branches innervating the geneoglossus muscle (the tongue's primary protruder muscle) has been shown to increase airflow in persons with OSA (Eiesel et al., "Direct hypoglossal nerve stimulation in obstructive sleep apnea," *Arch Otolaryngol Head Neck Surg*, vol. 123, pp. 57-61, 1997; Eiesel et al., "Tongue neuromuscular and direct hypoglossal nerve stimulation for obstructive sleep apnea," *Otolaryngol Clin North Am*, vol. 36, pp. 501-10, 2003; Schwartz et al., "Electrical stimulation of the lingual musculature in obstructive sleep apnea," *J Appl Physiol.*, vol. 81, pp. 643-652, 1996; Schwartz et al., "Therapeutic electrical stimulation of the hypoglossal nerve in obstructive sleep apnea," *Arch. Otolaryngol Head Neck Surg*, vol. 127, pp. 1216-1223, 2001; Oliven et al., "Sublingual electrical stimulation of the tongue during wakefulness and sleep," *Respir Physiol*, vol. 127, pp. 217-26, 2001; Oliven et al., "Upper airway response to electrical stimulation of the genioglossus in obstructive sleep apnea," *J Appl Physiol*, vol. 95, pp. 2023-9, 2003). Oliven et al. (2001, 2003) applied the sublingual stimulation through electrodes with large surface areas (conductive rubber) using biphasic, voltage-controlled pulses at 50 Hz and 200 μs/ph. The stimulation produced extension of the tongue and increased inspirational air flow rate in patients with OSA but did not produce arouser from sleep, as determined by the electroencephalogram. During sublingual electrical stimulation, inspired airflow increased from 58±16 ml/sec to 270±35 ml/sec in patients with severe OSA. This range of flow rates was still slightly below that of normal subjects during sleep (319±24 ml/sec). Unfortunately oxyhemoglobin desaturation was not measured in these subjects. However, in subjects without OSA, autonomic cardiovascular responses and arousal from sleep were triggered only when inspired air flow dropped below about 200 ml/sec, while mild airway obstruction had no effect (O'Donnell et al., "The effect of upper airway obstruction and arousal on peripheral arterial tonometry in obstructive sleep apnea," *Am J Respir Crit Care Med*, vol. 166, pp. 965-71, 2002).

Schwartz et al. (1996) determined that electrical stimulation of tongue protruder muscles increased airflow in OSA patients, while stimulation of tongue retractors decreased air flow. However Oliven et al. (2001) found that electrical stimulation of the posterior and also of the anterior surface of the tongue was more effective in increasing airflow than was electrical stimulation of the anterior surface alone, which nonetheless produced preferential activation of the of the geneoglossus muscle, and thus the greatest protrusion of the tongue. This suggests that the increased stiffness of the tongue induced by the electrical stimulation of antagonistic muscles (retractors and protruders) decreased $P_{crit}$ (Oliven et al., "Upper airway response to electrical stimulation of the genioglossus in obstructive sleep apnea," *J Appl Physiol*, vol. 95, pp. 2023-9, 2003) and this action was at least as important as the tongue protrusion per se in preventing collapse of the upper airway during sleep. Indeed, there have been conflicting reports as to whether passive extension of the flaccid tongue by retaining devices is effective in treating OSA (Rose et al., "Orthodontic procedures in the treatment of obstructive sleep apnea in children," *J Orofac Orthop*, vol. 67, pp. 58-67, 2006; Higurashi et al., "Effectiveness of a tongue-retaining device," *Psychiatry Clin Neurosci*, vol. 56, pp. 331-2, 2002). In patients with OSA, the sublingual stimulation caused a decrease in $P_{crit}$ during sleep whether the obstruction was in the velopharynx or in the oropharaynx, just as did electrical stimulation of the trunk of the hypoglossal nerve itself. This is an important observation since either or both regions may collapse during OSA. It is notable that these studies were conduced with nasal breathing, with the inspired air passing behind, rather than over, the tongue.

Oliven et al. (2003) found that electrical stimulation of the geneoglossus and associated muscles decreased $P_{crit}$ by an average of 3.18 cm $H_2O$ in persons with OSA. By way of comparison, Smith et al. (1988) measured $P_{crits}$ of 1 to 10 cm $H_2O$ in 6 persons with OSA, but in 5 of the 6 patients, $P_{crit}$ was between 1 and 2.7 cm $H_2O$. This, and the finding that airflow rates in these OSA patients increased to 270±35 ml/sec suggests that sublingual stimulation, and/or an approach that induces reflex activation of tongue protruder muscles with some co-activation of tongue retractors muscles, should prevent airway collapse in a significant fraction of OSA patients, provided that their $P_{crit}$ is not extremely high. However, sublingual electrical stimulation was in most cases not able to open the airway during complete apnea (Oliven et al., "Sublingual electrical stimulation of the tongue during wakefulness and sleep," *Respir Physiol*, vol. 127, pp. 217-26, 2001). This important finding illustrates the potential value of a "proactive" approach of the type proposed herein by the inventor, in which the electrical stimulation is applied when the tongue just begins to retract and loose muscle tone, and to initiate activation of tongue musculature before the airway actually becomes occluded.

SUMMARY OF THE INVENTION

The following embodiments and aspects thereof are described and illustrated in conjunction with compositions and methods which are meant to be exemplary and illustrative, not limiting in scope.

One embodiment of the present invention provides an apparatus, comprising: a sensor to monitor the position of a tongue and/or the force exerted by the tongue against the sensor; and one or more electrodes to deliver electrical stimuli to the ventral surface of the tongue. The apparatus may further comprise a dental fixture; for example, the sensor and the one or more electrodes may be mounted on the dental fixture. The apparatus may further comprise an electronic controller to translate a signal received from the sensor and to deliver an electrical stimulus comprising of a train of charge-balanced electrical pulses to the one or more electrodes. The apparatus may also further comprise a power source to deliver electricity to one or more components of the apparatus. The sensor of the apparatus may comprise an emitter and a detector in a transparent encapsulant separated by an opaque partition. The emitter may be an infrared emitter; the detector may be an infrared detector (e.g., phototransistor). The one or more electrodes may be attached to one or more flexible tubular carriers. The one or more electrodes may be also hemicylindrical in shape; for example, wrapped around the flexible tubular carriers. In various embodiments, the one or more electrodes may be about 5 to about 15 mm in length and about 3 to about 7 mm in width; about 8 to about 12 mm in length and about 4 to about 8 mm in width; and about 10 mm in length and about 5 mm in width. In other embodiments, the one or more electrodes may be about 10 mm A portion (e.g., distal portion) of the one or more electrodes may be adapted to allow contact with the ventral surface of the tongue.

Another embodiment of the present invention provides for a method to treat obstructive sleep apnea or to avoid an apneic or hypoxic episode in a subject, comprising: providing a sensor to monitor the position of a tongue and/or the force exerted by the tongue against the sensor, one or more electrodes to deliver electrical stimuli to the ventral surface of the tongue, an electronic controller to translate a signal received from the sensor and to deliver a train of electrical pulses to the one or more electrodes, and a power source to deliver electricity to the sensor, the one or more electrodes, and/or the electronic controller; sensing the position of the tongue and/or the force exerted by the tongue against the sensor; and causing electrical pulses to be delivered the ventral surface of the tongue via the one or more electrodes when the tongue is not in an anterior position, not in close proximity to the sensor, not touching the sensor and/or not exerting a prescribed force upon the sensor. The sensor and the one or more electrodes may be configured on a dental fixture. The electronic controller and/or the power source may also be configured on the dental fixture. The train of electrical pulses may have a voltage of about 5 to about 15 volts and a pulse frequency of about 3 to about 50 pulses per second. The prescribed force may be about 0 to about 150 gram(s). The lower value of 0 gram force allows for having the tongue position alone (i.e., merely contact with the sensor) in some users be adequate to maintain an open airway. In other embodiments, the prescribed force may be about 20 to about 100 grams.

Alternatively, the method may be a biofeedback method, whereby a defensive reflex is trained wherein the tongue moves anteriorly or dorsally in response to an onset of low-amplitude electrical stimulation. The train of electrical pulses may have a voltage of about 10 to about 25 volts and a pulse frequency of about 5 to about 50 pulses per second. The defensive reflex may be trained by applying cycles of low-amplitude electrical stimulation, increasing the amplitude of the electrical stimulation and terminating the electrical stimulation when the tongue moves anteriorly and contacts the sensor and/or when the tongue exerts a prescribed force against the sensor. The low-amplitude electrical stimulation may be one that is barely perceptible to the subject. The low-amplitude electrical stimulation encourages the subject to develop a protective reflex whereupon the tongue is moved into contact with the sensor and/or exerts a prescribed force against the sensor in order for the subject to avoid experience the uncomfortable, high-amplitude stimulation.

Another embodiment of the present invention comprises a system for treating obstructive sleep apnea, comprising: a sensor to monitor the position of a tongue and/or the force exerted by the tongue against the sensor; one or more electrodes to deliver electrical stimulus to the ventral surface of the tongue; an electronic controller to translate a signal received from the sensor and to deliver a train of electrical pulses to the one or more electrodes; and a power source to deliver electricity to the sensor, the one or more electrodes, and/or the electronic controller. The sensor and the one or more electrodes may be configured on a dental fixture. The sensor may comprise an emitter and a detector in a transparent encapsulant separated by an opaque partition. The emitter may be an infrared emitter; the detector may be an infrared detector (e.g., a phototransistor). The one or more electrodes may be attached to one or more flexible tubular carriers and the one or more electrodes may be hemicylindrical in shape; for example, the electrode may be wrapped around the flexible tubular carrier. In various embodiments, the one or more electrodes may be about 5 to about 15 mm in length and about 3 to about 7 mm in width; about 8 to about 12 mm in length and about 4 to about 8 mm in width; and about 10 mm in length and about 5 mm in width. A portion (e.g., distal) of the one or more electrodes may be adapted to allow contact with the ventral surface of a tongue.

Another embodiment of the present invention provides for an apparatus for the treatment of obstructive sleep apnea or for avoiding an apneic or hypoxic episode in a subject, comprising: means for sensing the position of a tongue and/or the force exerted by the tongue against the means for sensing; means for delivering electrical stimulus to the ventral surface of the tongue; means for translating a signal received from the sensing means and for delivering a train of electrical pulses to the means for delivering the electrical stimulus to the ventral surface of the tongue; and means for providing electricity to the apparatus.

Another embodiment of the present invention provides a computer readable medium having computer executable components for: monitoring the position of a tongue and/or the force exerted by the tongue against a sensor; translating a signal received from the sensor; and delivering a train of electrical pulses to the ventral surface of the tongue via one or more electrodes.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 2 depicts a block diagram of various components of the electronic controller in accordance with various embodiments of the present invention.

FIG. 5 depicts output from a sensor (lower trace) and the amplitude of the electrical stimulation (upper trace) in accordance with various embodiments of the present invention. A: Sensor and Controller operating in tongue position mode. B: Sensor operating in tongue position and force mode and Controller in tongue force mode.

DESCRIPTION OF THE INVENTION

Figure 1A:
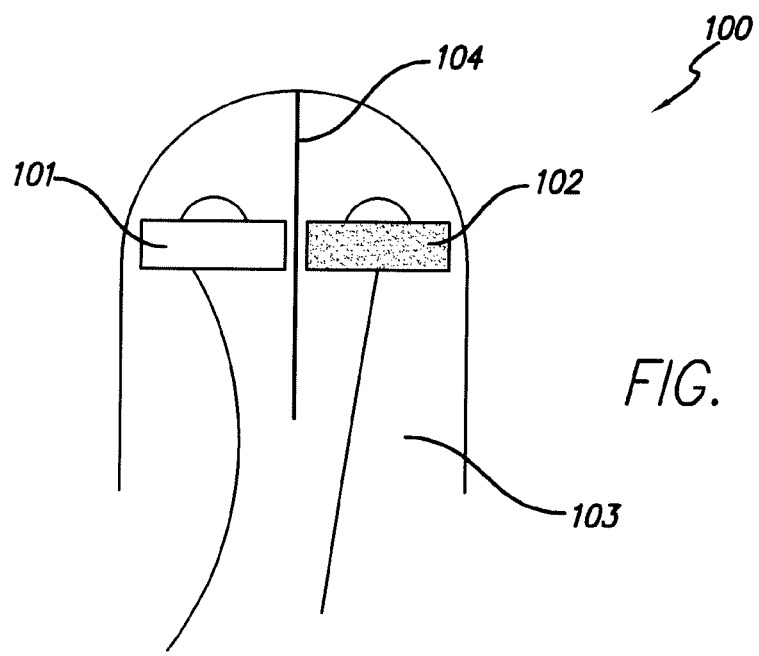
FIG. 1 depicts a schematic of a sensor that senses the tongue position and/or tongue force in accordance with various embodiments of the present invention. A: Side view; B: Top view.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Treatment" and "treating," as used herein refer to both therapeutic treatment and prophylactic or preventative measures, wherein the object is to prevent or decrease (lessen) the targeted condition or disorder even if the treatment or prevention is ultimately unsuccessful. Those in need of treatment include those already afflicted with the disorder as well as those prone to have the disorder or those in whom the disorder is to be prevented or treated. For example, in obstructive sleep apnea (OSA) treatment, a therapeutic apparatus may decrease the number of apneic and/or hypoxic episodes, which may decrease the symptoms and/or sequelae associated with OSA.

The obstruction of the upper airway in OSA is due to a reduction in the tone of the muscles of the upper airway during sleep, accompanied by the prolapse of the tongue base onto the airway. The collapse of the upper airway may be prevented by activation of the muscles that extend the tongue. Thus, various embodiments of the present invention provide for an apparatus, a system and a method for detecting the position of the tongue and/or the protrusion force exerted by the tongue against a sensor, and moving the tongue to the anterior position, maintaining the tongue in the anterior position and/or maintaining an ascribed amount of muscle tone in the tongue extensor muscles for the prevention, avoidance and/or treatment of obstructive sleep apnea.

In various embodiments of the present invention, apparatuses employ operant conditioning and/or direct electrical stimulation of branches of the motor nerves innervating muscles that protrude the tongue (e.g., branches of the hypoglossal nerve) to move the tongue to an anterior position, maintain the tongue in an anterior position, and/or maintain or increased tone in the tongue extensor muscles during sleep, thereby avoiding obstruction of the upper airway.

In one embodiment, the apparatus comprises a sensor to monitor the position of the tongue and/or the force exerted by the tongue (particularly, the tip of the tongue) against the sensor; and one or more electrodes to deliver electrical stimulus to the ventral surface of the tongue. The apparatus may further include a power source (e.g., external or battery) to deliver electricity to the apparatus. The apparatus may also further comprise an electronic controller to translate the signals from the sensor into a pattern of electrical pulses that are delivered to the one or more electrodes. The sensor is in electronic communication with the controller, which is in electronic communication with the one or more electrodes. The electronic communication may be made via conventional wiring or via wireless signals known in the art. To provide electricity to the apparatus, the power source is coupled to one or more of the following: the sensor, the one or more electrodes, and the controller.

Figure 1B:
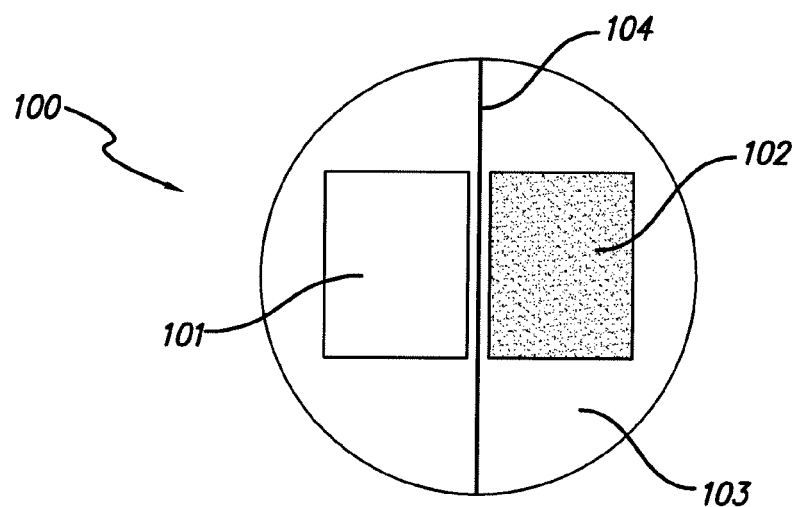

The sensor comprises an emitter and a detector. In one embodiment, as depicted in FIG. 1, the sensor comprises an emitter (e.g., infrared light-emitting diode (LED)) 101 and a detector (e.g., phototransistor) 102, both encapsulated in a biocompatible, transparent epoxy 103 (e.g., EpoTek 301 epoxy). The tongue position sensor is similar to glossometers that have been used in biofeedback systems to teach deaf children to speak (see e.g., Fletcher and McCutcheon, 1989). The detector 102 detects the intensity of pulsed infrared light that is back-scattered from the tongue. The circuitry is sensitive only to pulsed light from the emitter 101, to reduce interference from ambient room light. The intensity of the reflected signal at the sensor varies inversely to the distance between the tongue and the sensor. In one embodiment, the emitter 101 transmits the infrared light over a wide angle (e.g., approximately 160 degrees) and the detector 102 is sensitive over a similar wide angle. Thus, the infrared beam is reflected from a large area of the tongue, thereby reducing the tendency for the detector's output to be affected by differences in reflectivity from specific portions of the anterior surface of the tongue, when the orientations of the tongue change with respect to the detector. This allows monitoring the position of the tongue. The emitter 101 (e.g., LED) and the detector 102 (e.g., phototransistor) are in close proximity, separated only by a thin opaque partition 104. This proximity prevents loss of the backscattered infrared signal when the tongue is very close to, or in contact with, the sensor 100. The opaque partition, which extends to the surface of the hemispherical epoxy dome, prevents interference from light from the emitter that is reflected from the internal surface of the hemispherical dome. The partition also reduces interference from light reflected from a film of saliva that may be deposited on the dome. The dome's smooth surface and small radius of curvature (2 mm) also discourages accumulation of saliva.

When the tongue is in contact with the sensor, the sensor output will increase further when the tongue exerts pressure upon the hemispheric dome. The mechanism of the force-sensing mode is uncertain, but some versions of the glossometers used in speech therapy also have been reported to have this property. While not wishing to be bound by any particular theory, the inventor believes that it is due to volume reflection of the infrared emissions from the tissues within the translucent tongue. This signal increases with contact force, probably because reflection from the tongue's epithelium decreases with increasing contact pressure, while the partition between the LED and the phototransistor renders the sensor insensitive to reflection of the emitted infrared signal from the epithelium when the tongue is pressed against the sensor.

The sensor is adapted for mounting in the subject's mouth. In one embodiment, the sensor is adapted for mounting behind the subject's teeth. Particularly useful is having the sensor adapted for mounting behind the subject's lower incisor teeth. In a specific embodiment, the sensor is mounted on a dental fixture adapted for attaching to the lingual surface of the lower teeth.

Figure 3:
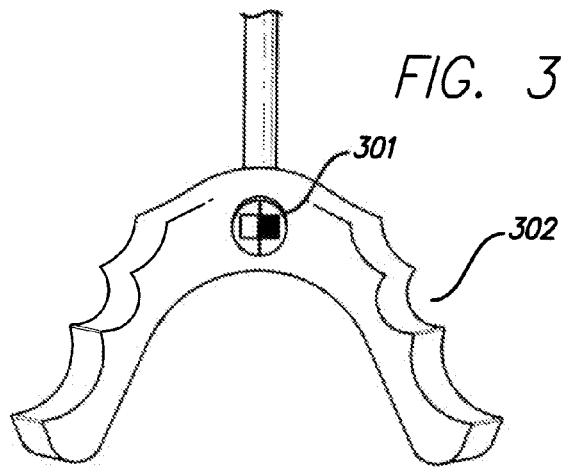
FIG. 3 depicts a sensor on a dental fixture in accordance with various embodiments of the present invention.

In one embodiment, as depicted in FIG. 3, a sensor 301 to detect the position of the tongue is provided. The sensor also may be mounted on a dental fixture 302 that attaches to the lingual surface of the lower teeth (see FIG. 3).

Figure 4A:
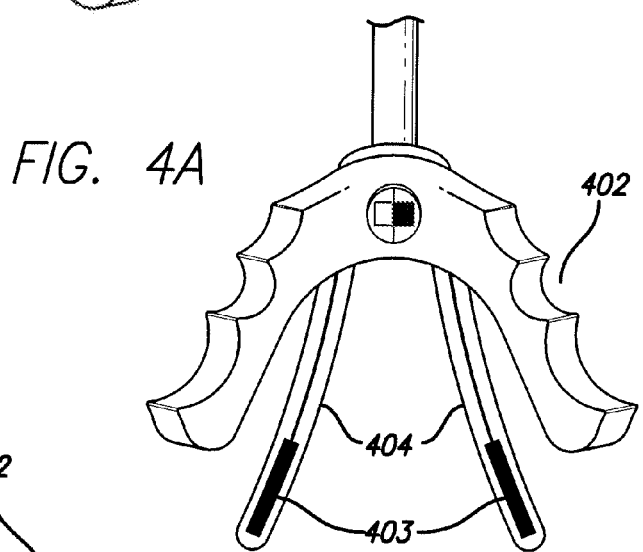
FIG. 4 depicts a sensor and stimulating electrodes on their flexible silicone rubber carriers on a dental fixture in accordance with various embodiments of the present invention. 4A: Front view; 4B: Side view.
Figure 4B:
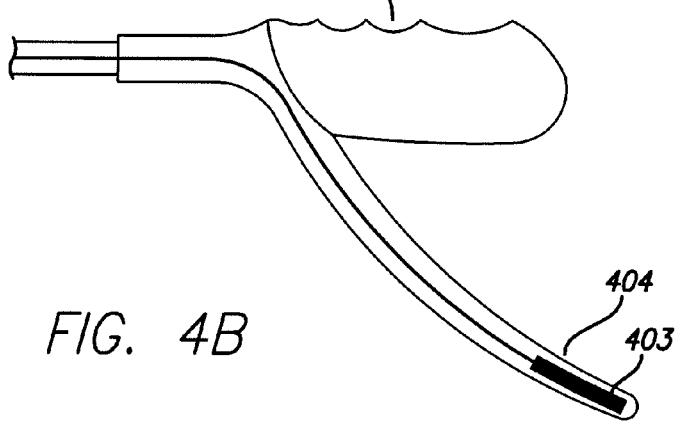

In one embodiment, as shown in FIG. 4, the electrodes 403 that deliver electrical stimulation to the tongue extensor muscles may be mounted on the posterior part of the dental fixture 402. In another embodiment, the electrodes may be attached to flexible cylindrical carriers 404. The carriers may be composed of silicone rubber. The carriers' flexibility enables the electrodes to maintain contact with the ventrolateral surface of the tongue as the tongue moves about in the mouth, without causing the user discomfort. The electrodes 403 may deliver electrical stimulus bilaterally to the ventrolateral surface of the tongue. The electrodes 403 may be made of any appropriate material known in the art. In one embodiment, the electrodes may comprise platinum. The dental fixture 402 may be acrylic and may be a custom dental fixture made for each individual subject.

In one particular embodiment, the sublingual stimulating electrodes 303 are hemi-cylinders of platinum foil, a metal which is stable in biological fluid and will not undergo electrolytic decomposition during prolonged electrical stimulation. Other metals commonly used to deliver electrical stimulation may be used; for example, alloys comprising various proportions of platinum and iridium, or platinum or platinum/iridium alloys coated with various forms of iridium oxide, including anodically-formed iridium oxide film (AIROF) or putter-coated iridium oxide (SIROF). The hemi-cylinders are molded onto silicon rubber tubes 404. The platinum foil may be wrapped around the flexible carriers to form the hemicylindrical shape. In one embodiment, the segments (e.g., distal portion) of the flexible silicon rubber tubes expose the electrodes to allow contact with the ventral surface of the tongue. This configuration directs the stimulation medially and dorsally into the ventral surface of the tongue and to the nerve that innervates the tongue extensor muscles, including the geneoglossus muscle, and so that the stimulus does not spread into the jaw, and thereby activate pain fibers in the periodontal ligaments and teeth. With this precaution, the stimulus is noticeable but not uncomfortable, up to quite a high amplitude (e.g., 10 V with 50 Hz stimulation, 200 μs pulse duration, and a 50% duty cycle). In various embodiments, the one or more electrodes may be about 5 to about 15 mm in length and about 3 to about 7 mm in width; about 8 to about 12 mm in length and about 4 to about 8 mm in width; and about 10 mm in length and about 5 mm in width.

Figure 6:
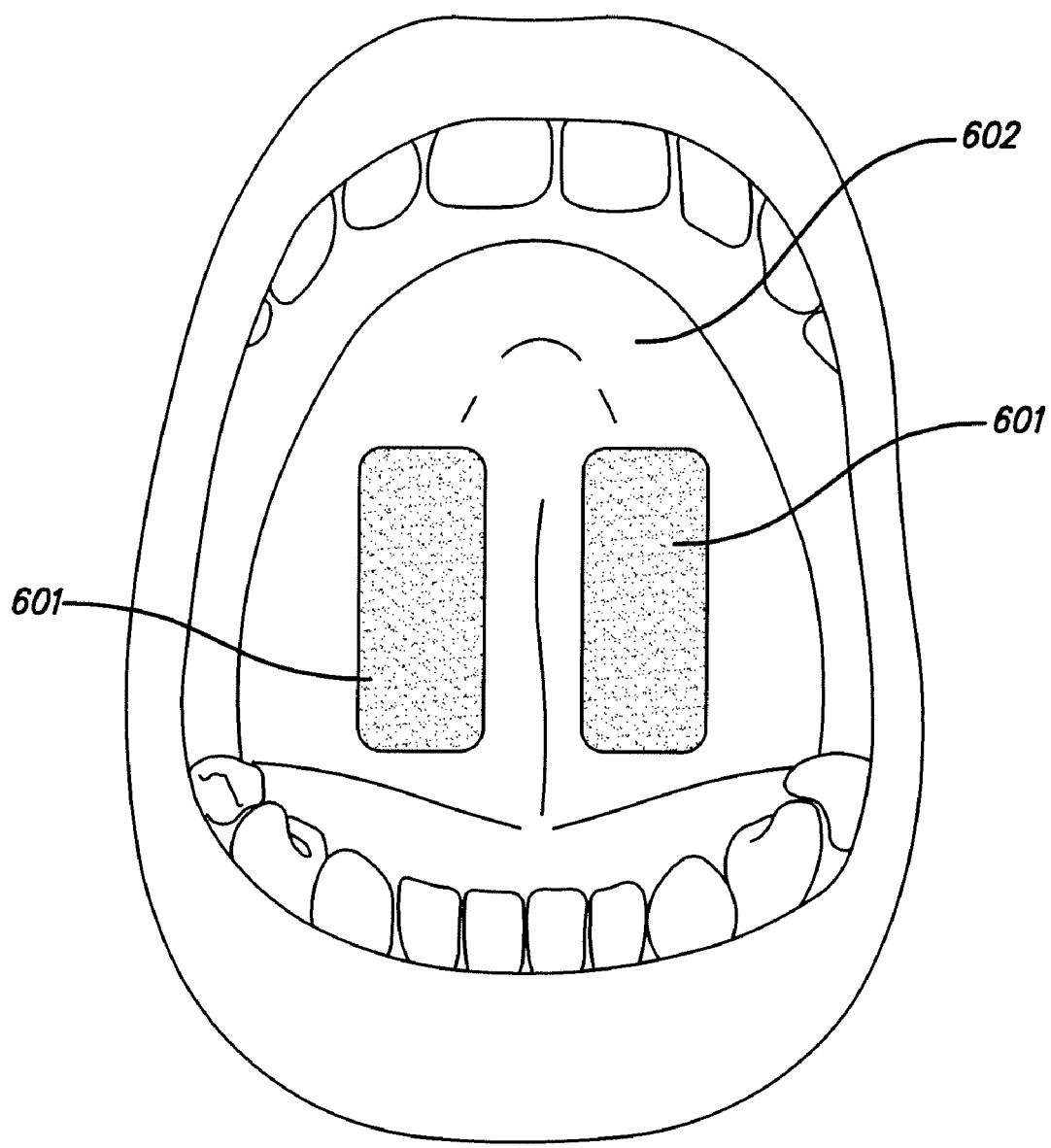
FIG. 6 depicts areas on the ventral side of the tongue in which the electrical stimulation may be applied in accordance with various embodiments of the present invention.

As shown in FIG. 6, areas 601 may be areas wherein the electrodes contact the ventral surface of the tongue 602 to deliver a train of electrical pulses in accordance with various embodiments of the present invention.

Figure 7:
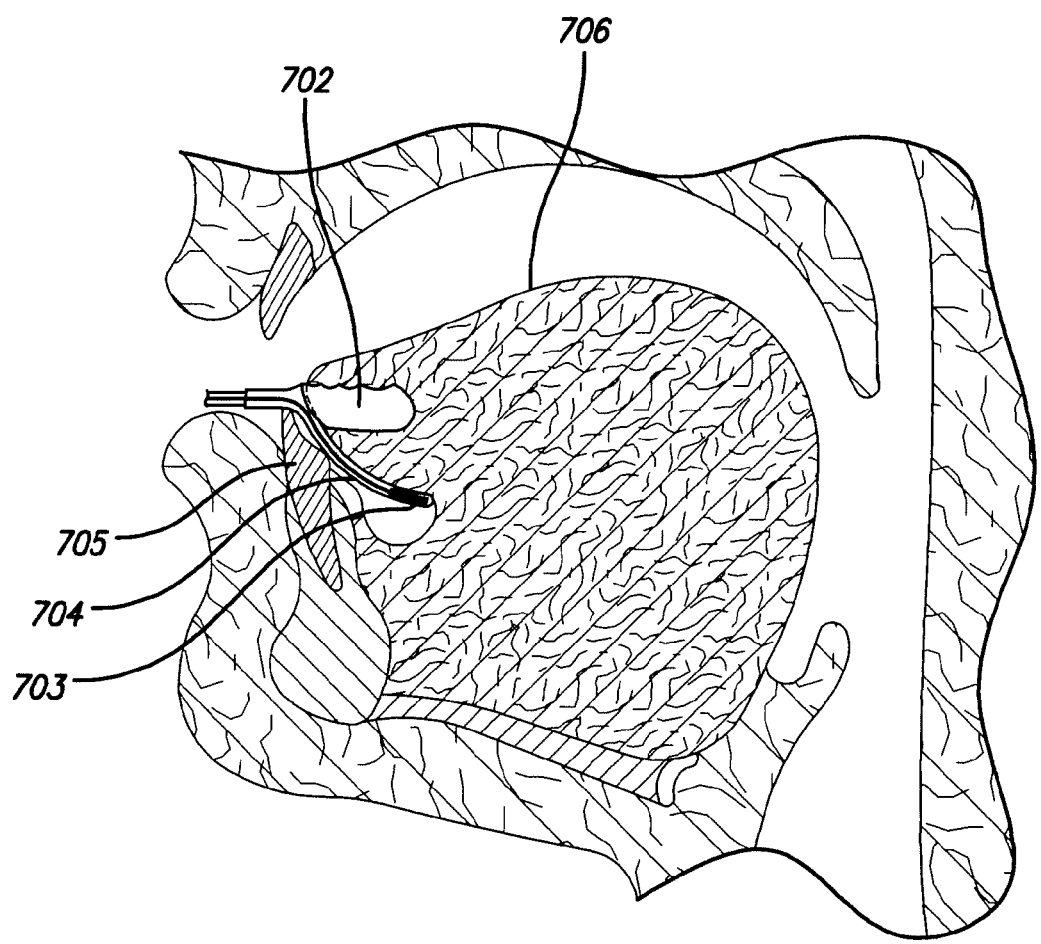
FIG. 7 depicts an apparatus of the present invention inside the mouth in accordance with an embodiment of the present invention.

FIG. 7 shows a side view of an apparatus as described herein in a subject's mouth. The dental fixture 702 is positioned on the lingual surface of the lower teeth 705. A portion of the flexible tubular carrier 704 with the electrode 703 is in contact with the ventral surface of the tongue 706.

Figure 8A:
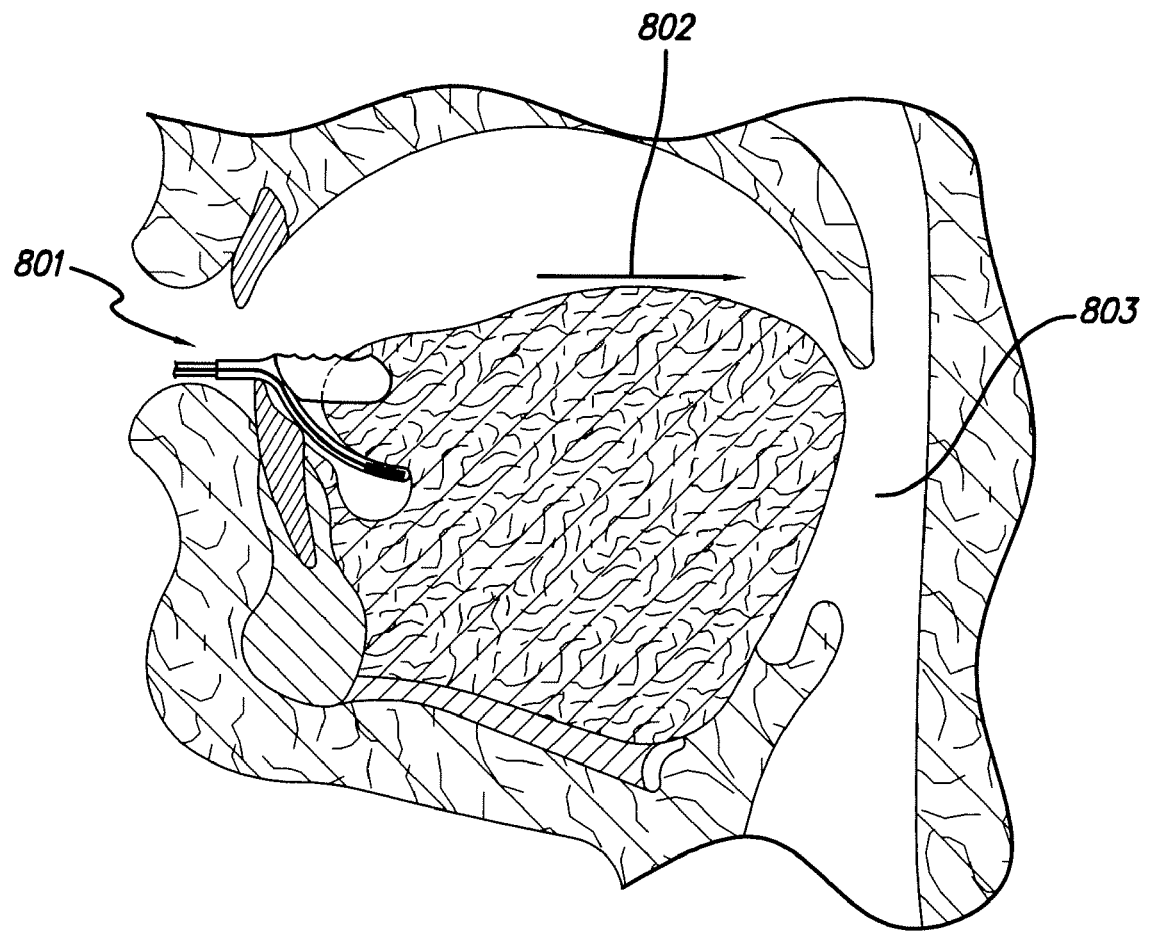
FIG. 8A shows an apparatus of the present invention inside the mouth with the tongue in a posterior position in accordance with an embodiment of the present invention.
Figure 8B:
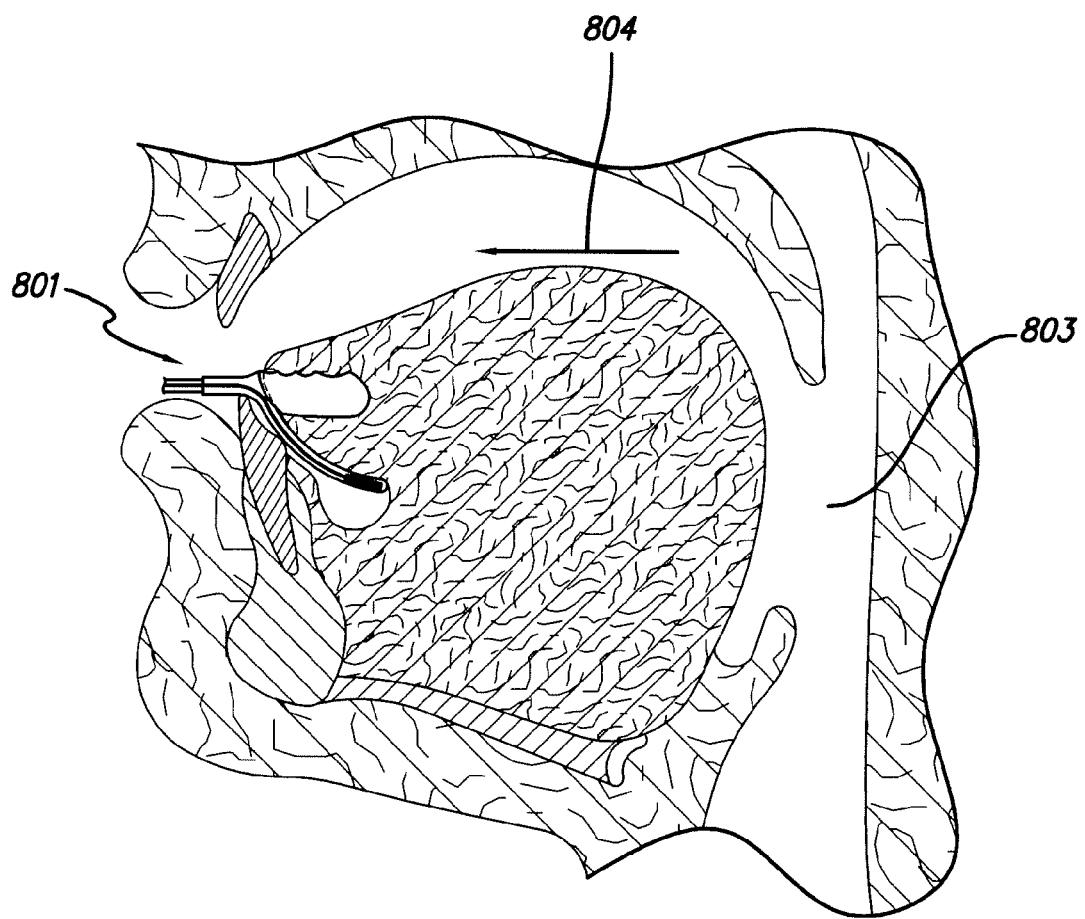
FIG. 8B shows an apparatus of the present invention inside of the mouth with the tongue moved to an anterior position after the delivery of electrical stimulation in accordance with an embodiment of the present invention.
Figure 9:
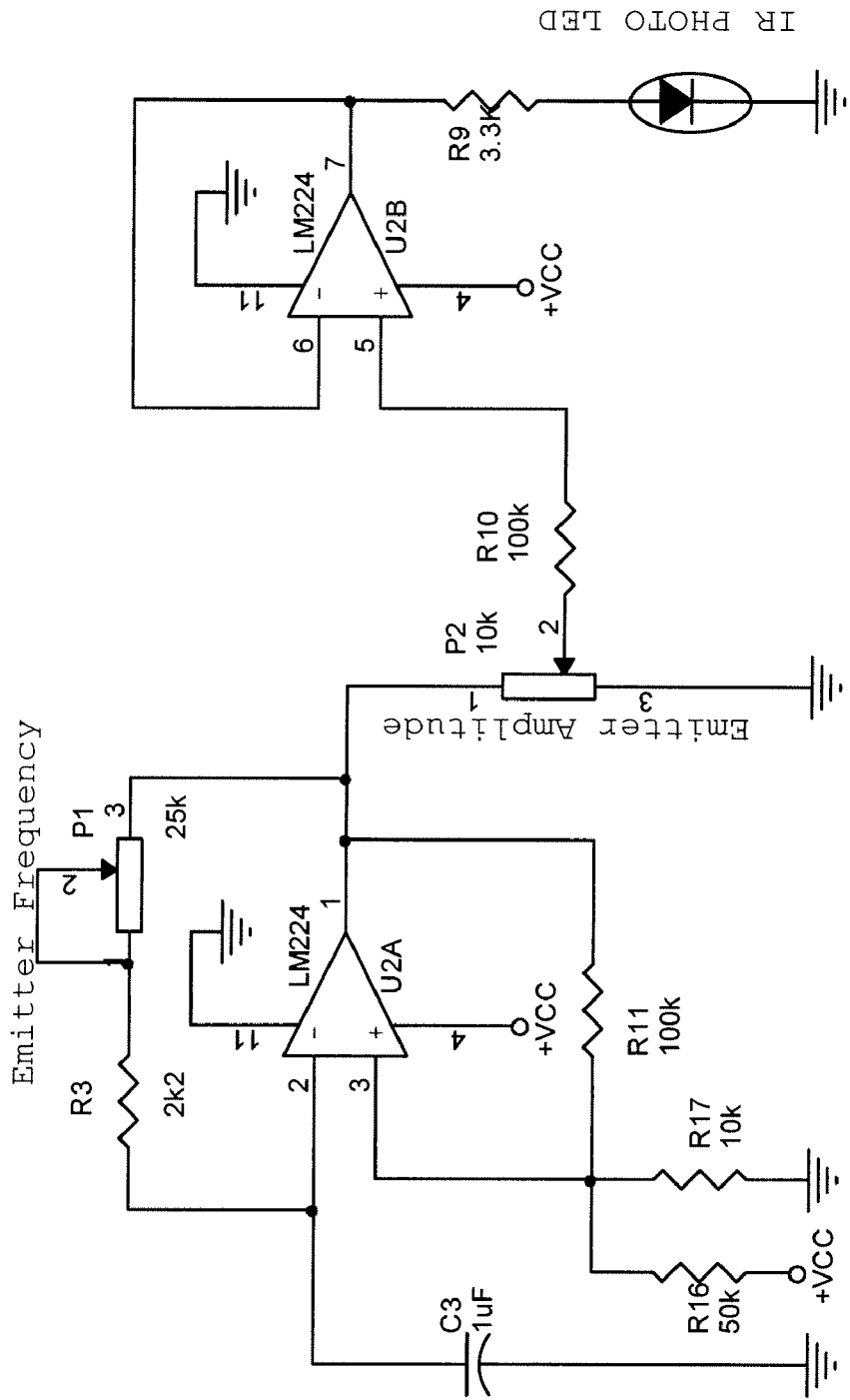
FIG. 9 depicts an emitter circuit in accordance with an embodiment of the present invention.

FIG. 8A shows a side view of an apparatus 801 as described herein in a subject's mouth wherein the tongue has moved 802 to a posterior position and may obstruct the airway 803. FIG. 8B shows a side view of an apparatus 801 as described herein in a subject's mouth wherein the tongue has moved 804 to an anterior position and is touching the sensor (not depicted) on the apparatus 804 and thus will not obstruct the airway 803.

FIG. 2 is a block diagram of various components of the electronic controller 200. The electronic controller 200 may include a programmable central processing unit (CPU) 230 which may be implemented by any known technology, such as a microprocessor, microcontroller, application-specific integrated circuit (ASIC), digital signal processor (DSP), or the like. The CPU 230 may be integrated into an electrical circuit, similar to a "motherboard" of a general purpose computer that supplies power to the CPU 230 and otherwise supports its function. The CPU 230 may include internal memory or memory 240 may be coupled thereto. The memory 240 is a computer readable medium that includes instructions or computer executable components that are executed by the CPU 230. The memory 240 may be coupled to the CPU 230 by an internal bus 250.

The memory 240 may comprise random access memory (RAM) and read-only memory (ROM). The memory 240 contains instructions and data that control the operation of the CPU 230. The memory 240 may also include a basic input/output system (BIOS), which contains the basic routines that help transfer information between elements within the electronic controller 200. The present invention is not limited by the specific hardware component(s) used to implement the CPU 230 or memory 240 components of the electronic controller 200.

The electronic controller 200 may also include an external device interface 260 permitting the user or a medical professional to enter control commands, such as a command triggering the delivery of the electrical pulses, commands providing new instructions to be executed by the CPU 230, commands changing parameters related to electrical pulses delivered by the electronic controller 200, and the like, into the electronic controller 200. The external device interface 260 may include a wireless user input device. The external device interface 260 may include an antenna (not shown) for receiving a command signal, such as a radio frequency (RF) signal, from a wireless user input device such as a computer-controlled programming wand. The electronic controller 200 may also include software components for interpreting the command signal and executing control commands included in the command signal. These software components may be stored in the memory 240.

The electronic controller 200 includes an interface 212 coupled to the sensor 210 for receiving signals regarding the position of the tongue or the force exerted by the tongue onto the sensor. The signal interface 212 may include any standard electrical interface known in the art for connecting a signal carrying wire to a conventional circuit board as well as any components capable of communicating a low voltage time varying signal received from the sensor 210 through an internal bus 214 to the CPU 230. The signal interface 212 may include hardware components such as memory as well as standard signal processing components such as an analog to digital converter, amplifiers, filters, and the like.

The electronic controller 200 includes an electrical signal interface 222 coupled to electrodes 220A and 220B for delivering the electrical stimulation pulses to the tongue to stimulate a branch of the hypoglossal nerve. The electrical signal interface 222 may include any standard electrical interface known in the art for connecting a signal-carrying wire to a conventional circuit board as well as any components capable of communicating a low voltage time-varying signal generated by the CPU 230 or a signal generating device controlled by the CPU 230 to the electrodes 220A and 220B through an internal bus 252. The exogenous electrical signal interface 222 may include hardware components such as memory as well as standard signal processing components such as a digital to analog converter, amplifiers, filters, and the like.

The various components of the electronic controller 200 may be coupled together by the internal buses 214, 250, 252, and 254. Each of the internal buses 214, 250, 252, and 254 may be constructed using a data bus, control bus, power bus, I/O bus, and the like.

The electronic controller 200 may include instructions 280 executable by the CPU 230 for processing and/or analyzing the signals received by the sensor 210. Additionally, the electronic controller 200 may include instructions 280 executable by the CPU 230 for generating an exogenous electrical signal delivered to a branch of the hypoglossal nerve by the electrodes 220A and 220B. These instructions may include computer readable software components or modules stored in the memory 240.

The controller also may be fabricated using discrete logic components and analog circuit elements. FIGS. 9-17 depict examples of the circuit elements and these examples are further described below. FIG. 16 depicts the control and stimulation circuit that are separately shown by FIGS. 9-15.

Other embodiments of the present invention provide for methods to prevent and/or treat obstructive sleep apnea. In various embodiments, the method involves moving the tongue anteriorly before it has moved sufficiently posteriorly so as to begin to obstruct the upper airway. In other embodiments, the method involves moving the tongue anteriorly even after it has moved sufficiently posteriorly to obstruct the upper airway.

In one embodiment, the method comprises obliging the tongue to move anteriorly by stimulation of branches of the motor nerves innervating muscles that protrude the tongue. The method comprises using an apparatus as described herein.

When the sensor detects that the tongue is not in an anterior position and particularly in its most anterior position, the electronic controller begins to deliver charge-balanced, pulsatile electrical stimulation through the electrodes. Alternatively, the apparatus may be adjusted to begin the electrical stimulation whenever the tongue is not exerting a prescribed amount of force upon the sensor. For example, the tongue exertion force against the sensor to terminate stimulation may be about 0 to about 150 gram(s). The lower value of 0 gram force allows for having the tongue position alone (i.e., merely contact with the sensor) in some users be adequate to maintain an open airway. In other embodiments, the prescribed force may be about 20 to about 100 grams. This mode may also be used when it is determined that additional tone in the tongue muscles is required to prevent the obstruction of the airway.

Initially, the amplitude of the stimulus pulses is very low and imperceptible to the user, but if the tongue remains retracted from the sensor (e.g., in a posterior position) or does not exert the prescribed force upon the sensor, the amplitude increases steadily (e.g., over an interval of 10 to 20 seconds and the rate of increase is adjustable), becoming perceptible as a light tactile sensation, and then becoming mildly uncomfortable as the amplitude increases due to strong stimulation of the sensory nerves in the lingual mucosus. The amplitude and pulse rate of the electrical stimulus may be adjusted so that the most intense sensation experienced by the user will be mildly noxious but tolerable. In various embodiments, the parameters of electrical stimulation are about 5 to about 15 volts and about 3 to about 50 pulses per second (e.g., mode 1). In other embodiments, the parameters of electrical stimulation are about 10 to about 25 volts and about 5 to about 50 pulses per second (e.g., mode 2). It is expected that this will encourage the user to develop a protective reflex whereupon the tongue is moved into contact with the sensor and/or exerts a prescribed force upon the sensor in response to the onset of the stimulus when the stimulus amplitude is very low. The tongue moves dorsally and/or anteriorly in response to direct excitation of branches of the hypoglossal nerve which innervates the geneoglossus muscle that protrudes the tongue. The movement may be volitional, by reflex, directly due to the electrical stimulation of the motor nerve or any combination thereof. The user may still retain volitional control of the tongue. The stimulus amplitude remains below the charge density which can cause tissue injury. When the tongue is moved anteriorly and makes contact with the sensor or exerts a prescribed force against the sensor, the electrical stimulation may cease.

FIG. 5 shows the output from the sensor (lower trace) and the amplitude of the electrical stimulation (upper trace), which is initiated and terminated when the sensor output falls below and rises above a specified value.

The gain of the infrared sensor can be adjusted so that it is able to monitor tongue force applied to its surface, as well as tongue position, and the electronics can be set to initiate the electrical stimulus when the tongue relaxes the pressure against the sensor and terminate the stimulation when the tongue presses against the sensor (FIG. 5B).

In another embodiment, the method may be a biofeedback-based method. A biofeedback based method may generate, in a subject, a conditioned defensive reflex whereby the tongue is moved anteriorly and/or dorsally in response to very weak, barely perceptible electrical stimulation delivered to the ventral surface of the tongue. This mode may be used alone or in combination with the mode wherein the movement of the tongue is affected directly by the electrical stimulation of branches of the hypoglossal nerve.

There is a direct and sequential relation between the barely perceptible low-amplitude stimulation, the subsequent mildly uncomfortable high amplitude simulation and termination of the stimulation when the tongue moves anteriorly. Thus, it may condition a defensive reflex whereby the tongue moves forward in response to the onset of the barely perceptible low-level (e.g., low amplitude) stimulation. This conditioned training may be developed and maintained by appropriate training when the subject is awake. Also, it may be maintained when the subject is asleep. While not wishing to be bound by any particular theory, the inventor believes that the conditioned reflex will persist during sleep, in response to a level of electrical stimulation that will not disturb sleep, because this is true of other protective oral reflexes, including opening of the jaw and retraction of the tongue in response to light bite pressure against the tongue.

Additional embodiments of the present invention provide for systems for the prevention and/or treatment of obstructive sleep apnea.

In one embodiment, the system comprises a sensor to monitor the position of the tongue and/or the force exerted by the tongue, particularly, the tip of the tongue, against the sensor; one or more electrodes to deliver electrical stimulus to the ventral surface of the tongue; an electronic controller to translate the signals from the sensor into a pattern of electrical pulses that are delivered to the one or more electrodes; and a power source to deliver electricity to one or more components of the system. The sensor is in electronic communication with the controller, which is in electronic communication with the one or more electrodes. To provide electricity to the system, the power source is in electronic communication with one or more of the following: the sensor, the one or more electrodes, the controller.

Another embodiment of the present invention provides for an apparatus for the treatment of obstructive sleep apnea or for avoiding an apneic or hypoxic episode in a subject, comprising: means for sensing the position of a tongue and/or the force exerted by the tongue against the means for sensing; means for delivering electrical stimulus to the ventral surface of the tongue; means for translating a signal received from the sensing means and for delivering a train of electrical pulses to the means for delivering the electrical stimulus to the ventral surface of the tongue; and means for providing electricity to the apparatus.

Another embodiment of the present invention provides a computer readable medium having computer executable components for: monitoring the position of a tongue and/or the force exerted by the tongue against a sensor; translating a signal received from the sensor; and delivering a train of electrical pulses to the ventral surface of the tongue via one or more electrodes.

EXAMPLE

The following example is provided to better illustrate various embodiments of the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

The Emitter Circuit (FIG. 9) generates the waveform that drives the infrared light-emitting diode (LED) of the tongue position sensor. It generates a square wave voltage signal ranging in frequency from 100 Hz to 1 KHz (set by potentiometer P1). The duty cycle of the signal is low (10%) to reduce power consumption and prolong battery life.

Figure 10:
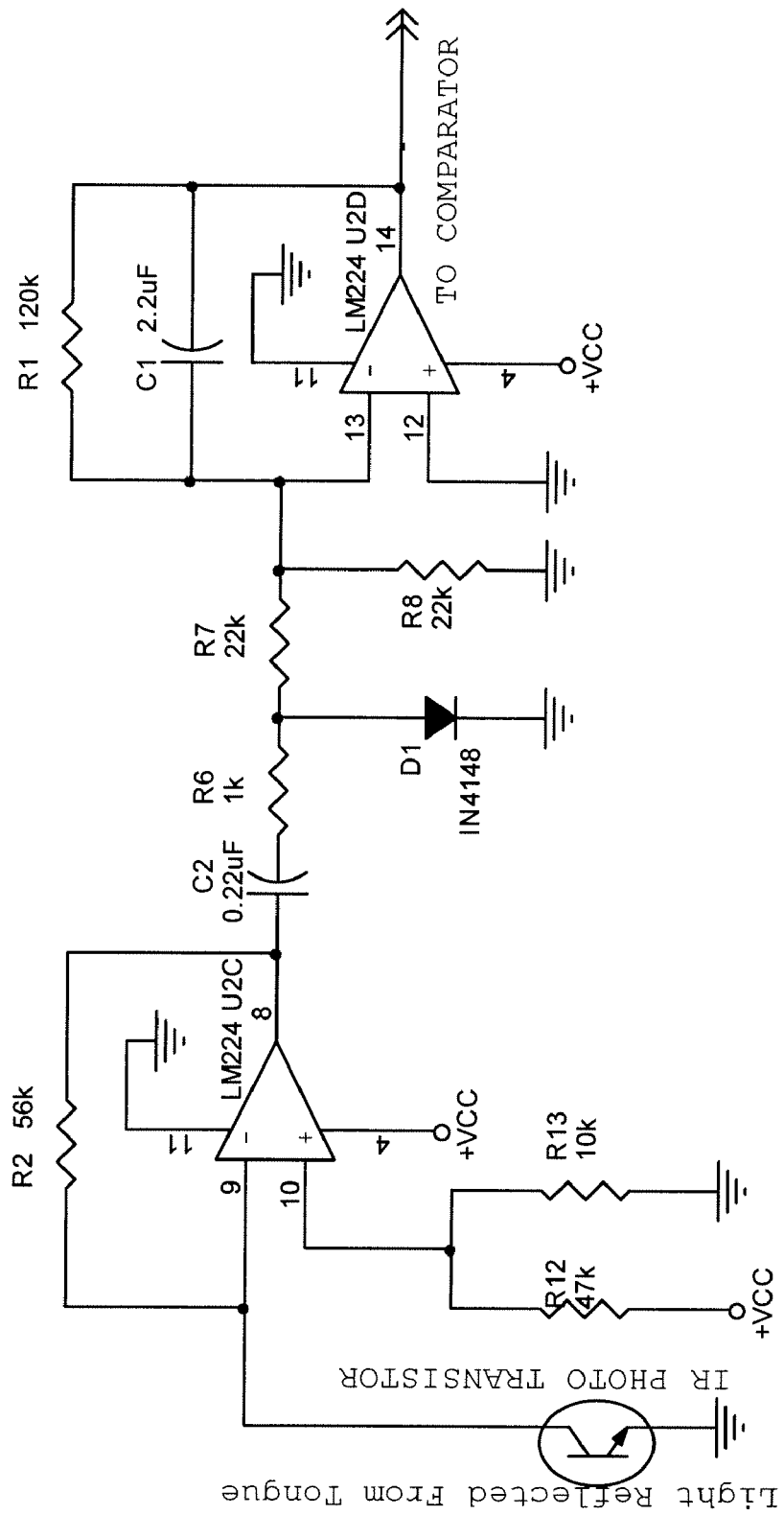
FIG. 10 depicts a detector circuit in accordance with an embodiment of the present invention.
Figure 11:
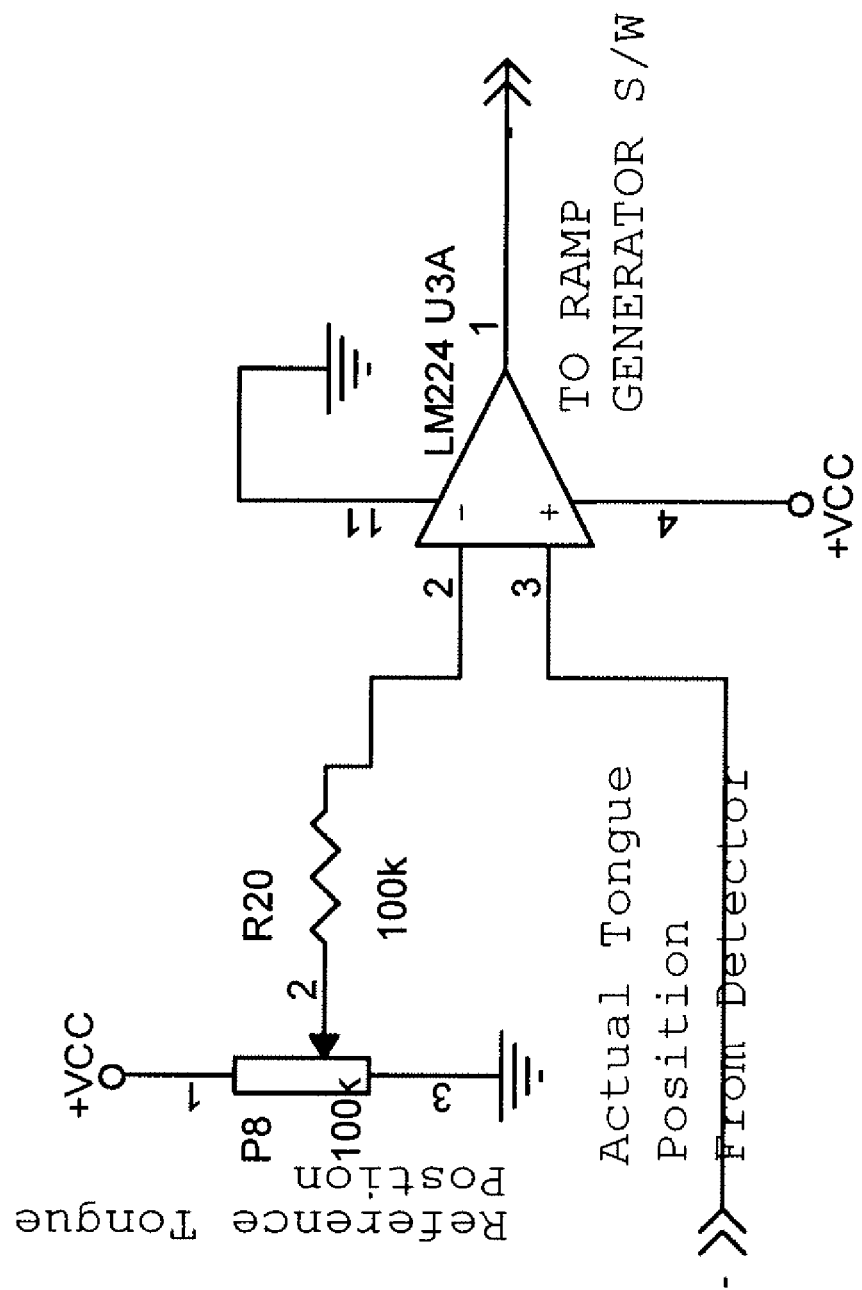
FIG. 11 depicts a comparator circuit in accordance with an embodiment of the present invention.

A detector circuit is shown in FIG. 10. The pulsed Infrared light is emitted from the LED and the light reflected from the tongue is detected by the infrared (IR) phototransistor and used to determine the tongue position. The use of pulsed light signals reduces interference from ambient light when the user's mouth is partly open. The IR phototransistor is biased to operate in photo-conductive mode. The signal from the phototransistor includes a component that is proportional to the pulsed light signal reflected from the tongue and also may contain some low-frequency interference from environmental light. The second stage of the detector circuit if a high=pass filter that removes the low-frequency components and converts the high-frequency (pulsed) component into a voltage signal that is proportional to the reflected light intensity from the tongue. This signal is larger when the tongue is close to the sensor, and will increase further when the tongue applies force to the sensor.

The Comparator Circuit (FIG. 11) receives the tongue position signal from the detector and subtracts it from the "reference" tongue position signal, which is set by potentiometer P8. If the signal from the detector is less than the reference level, indicating that the tongue is retracted from the sensor, the comparator output switches off. By adjusting P8, the output can be made to turn on ("go high") either when the tongue contacts the sensor or when the tongue applied a prescribed amount of force against the sensor.

Figure 12:
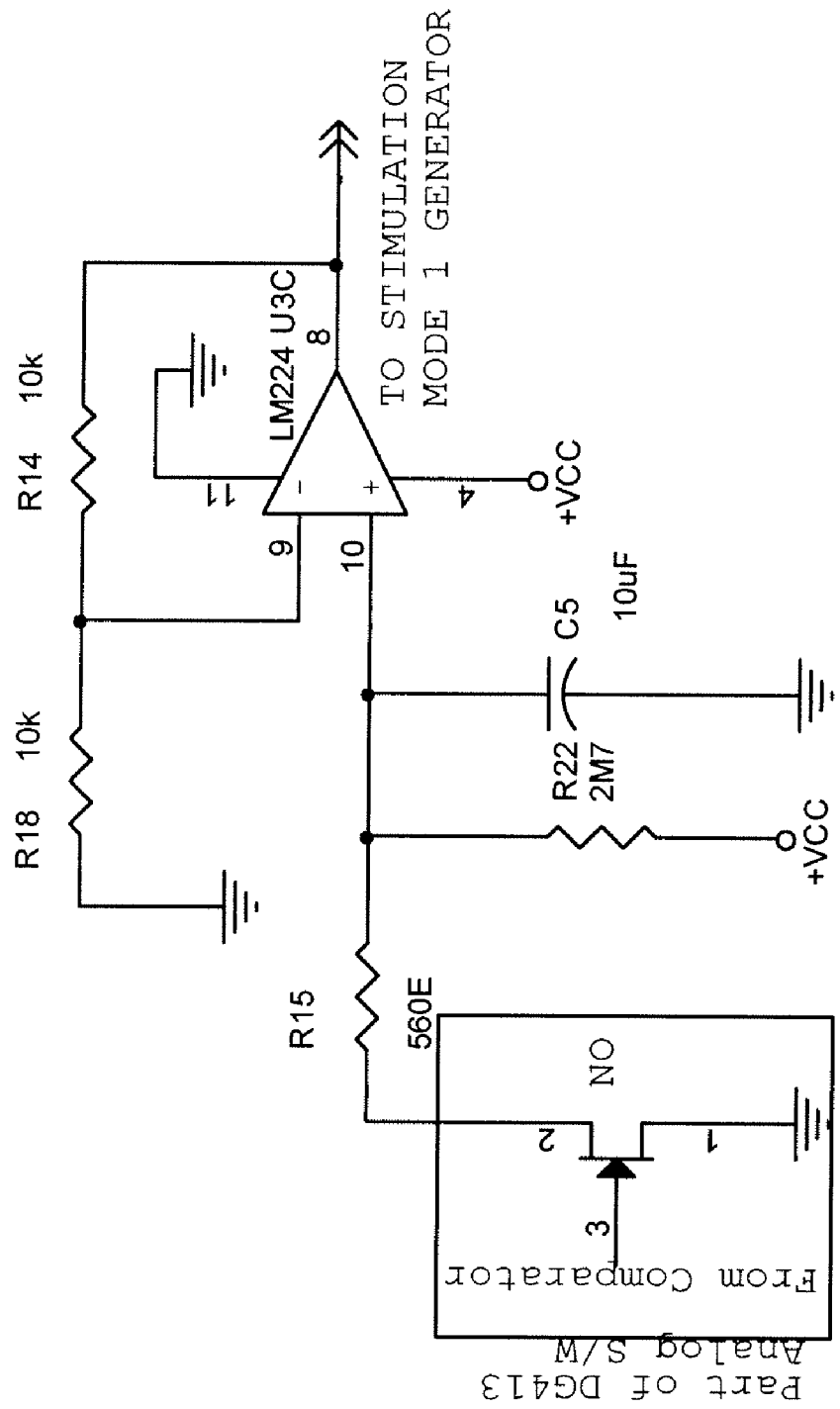
FIG. 12 depicts a ramp generator circuit in accordance with an embodiment of the present invention.

A ramp generator is shown in FIG. 12. The output from the comparator is fed to the stimulator ramp controller switch which connects resistor R15 to ground when the capacitor output is high. When the comparator output goes low indicating low signal from the sensor, the field-effect transistor ceases to conduct and capacitor C5 begins to charge, generating a steadily-increasing voltage (a voltage "ramp"). When the tongue again contacts the sensor, or exerts the prescribed force against the sensor the comparator output goes high and R15 is again shorted to ground, rapidly discharging C5 and resetting the ramp voltage to 0.

Figure 13:
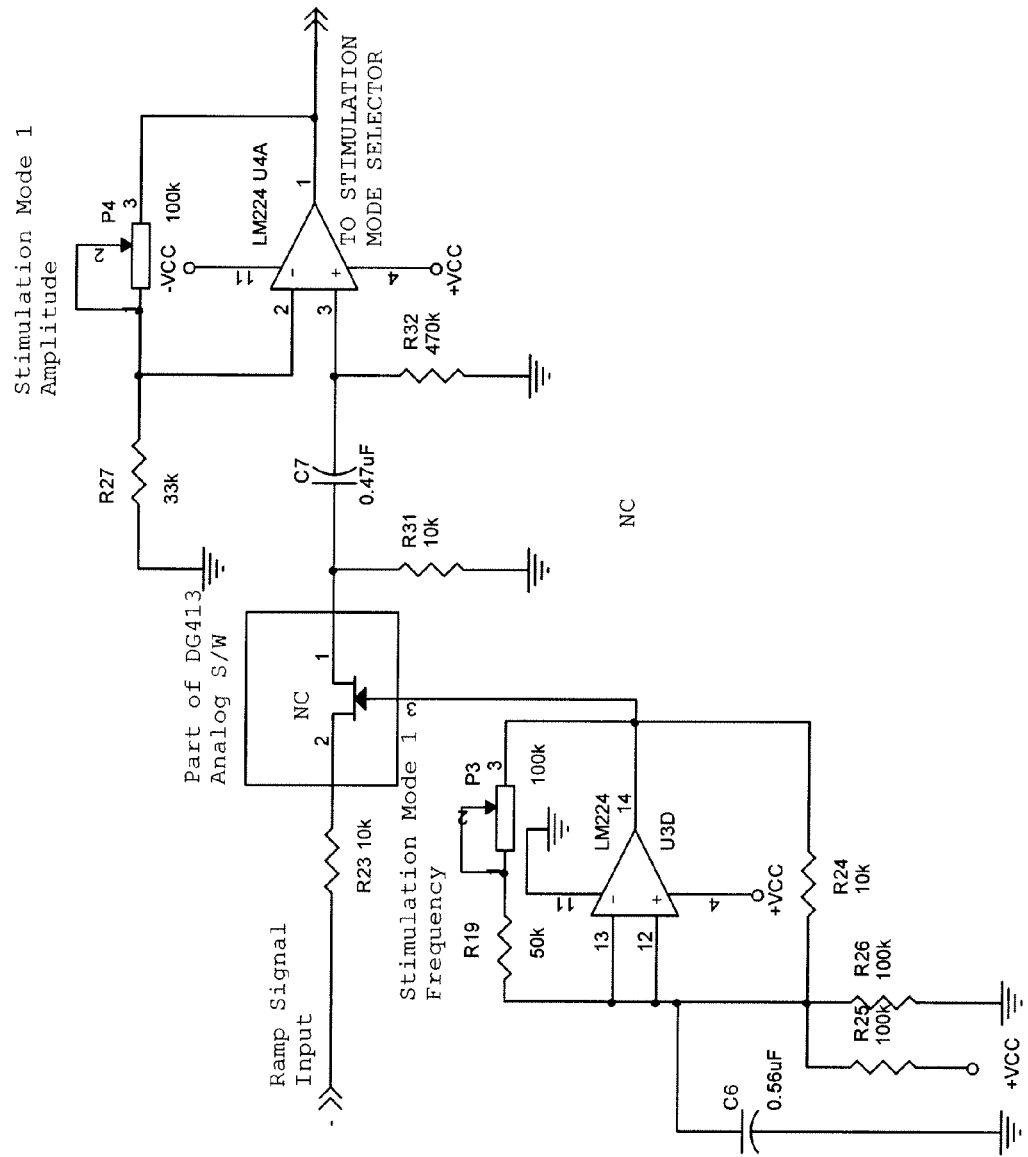
FIG. 13 depicts a mode 1 stimulation generator circuit in accordance with an embodiment of the present invention.

A Mode 1 stimulus generator is shown in FIG. 13. The ramp voltage from the integrator is fed to the input of the mode 1 stimulator, in which the ramp voltage is converted to a train of charge-balanced stimulus pulses whose amplitude is proportional to the amplitude of the ramp. The frequency of the stimulus pulses is set by P3 and the amplitude of the stimulus pulses is set by P4. These pulses are passed to the stimulator mode selector.

Figure 14:
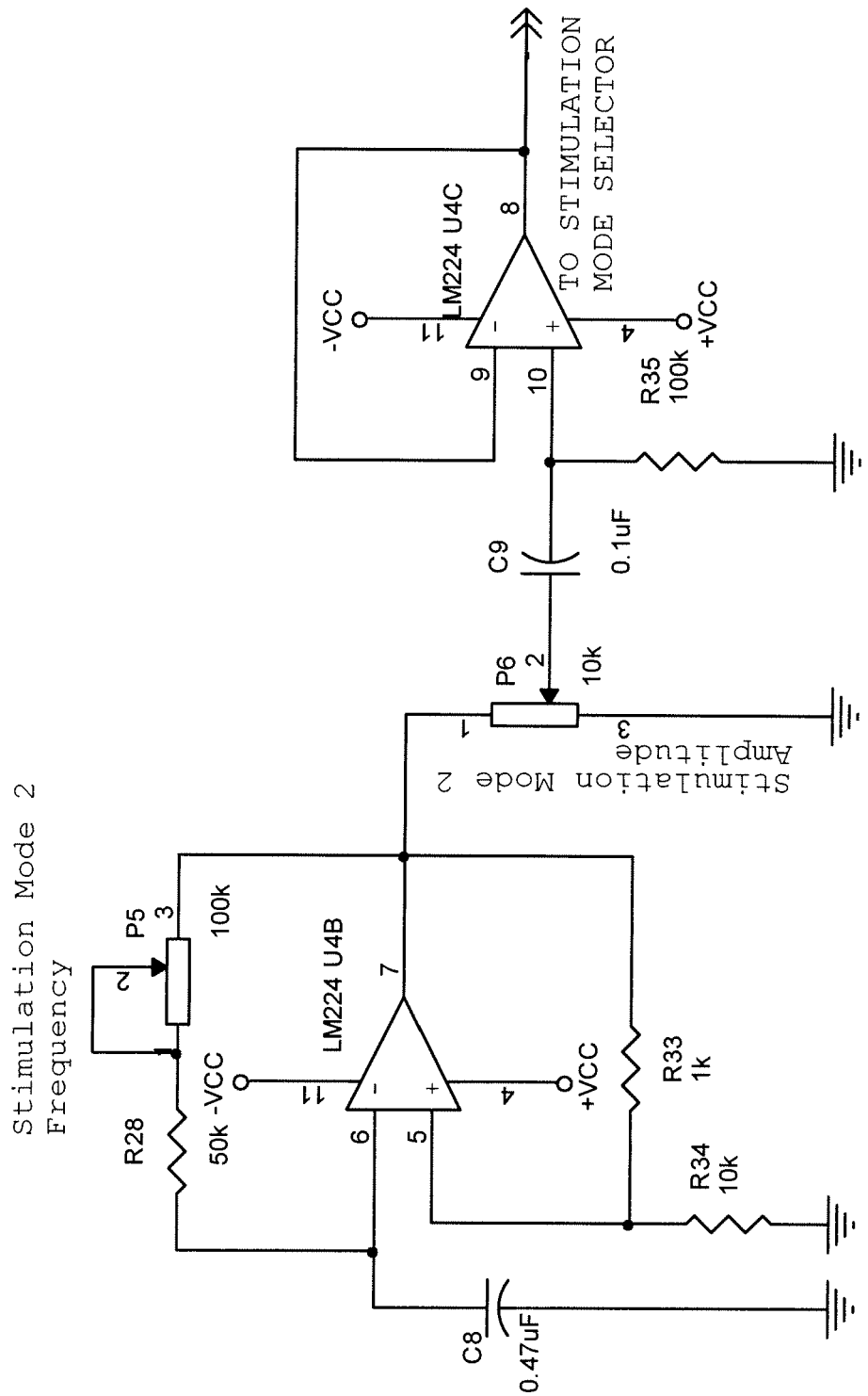
FIG. 14 depicts a mode 2 stimulation generator circuit in accordance with an embodiment of the present invention.

A Mode 2 stimulation generator is shown in FIG. 14. This is a high-rate stimulation that is intentionally mildly uncomfortable to the user and may be used to help to expedite the conditioning of the tongue-positioning reflex. However, depending on how various users respond to the mode 2 stimulation, its inclusion in the stimulation program may be optional and it may be omitted from the program by setting the mode-switching potentiometer P7 to a high level. The stimulation rate of mode 2 is set by potentiometer P5 and its amplitude by P6 of the mode 2 stimulator stage.

Capacitor C8 of the mode switching circuit ensures that the stimulus is charge-balanced, ensuring that the electrical stimulation does not produce pH changes at either of the stimulating electrodes.

Figure 15:
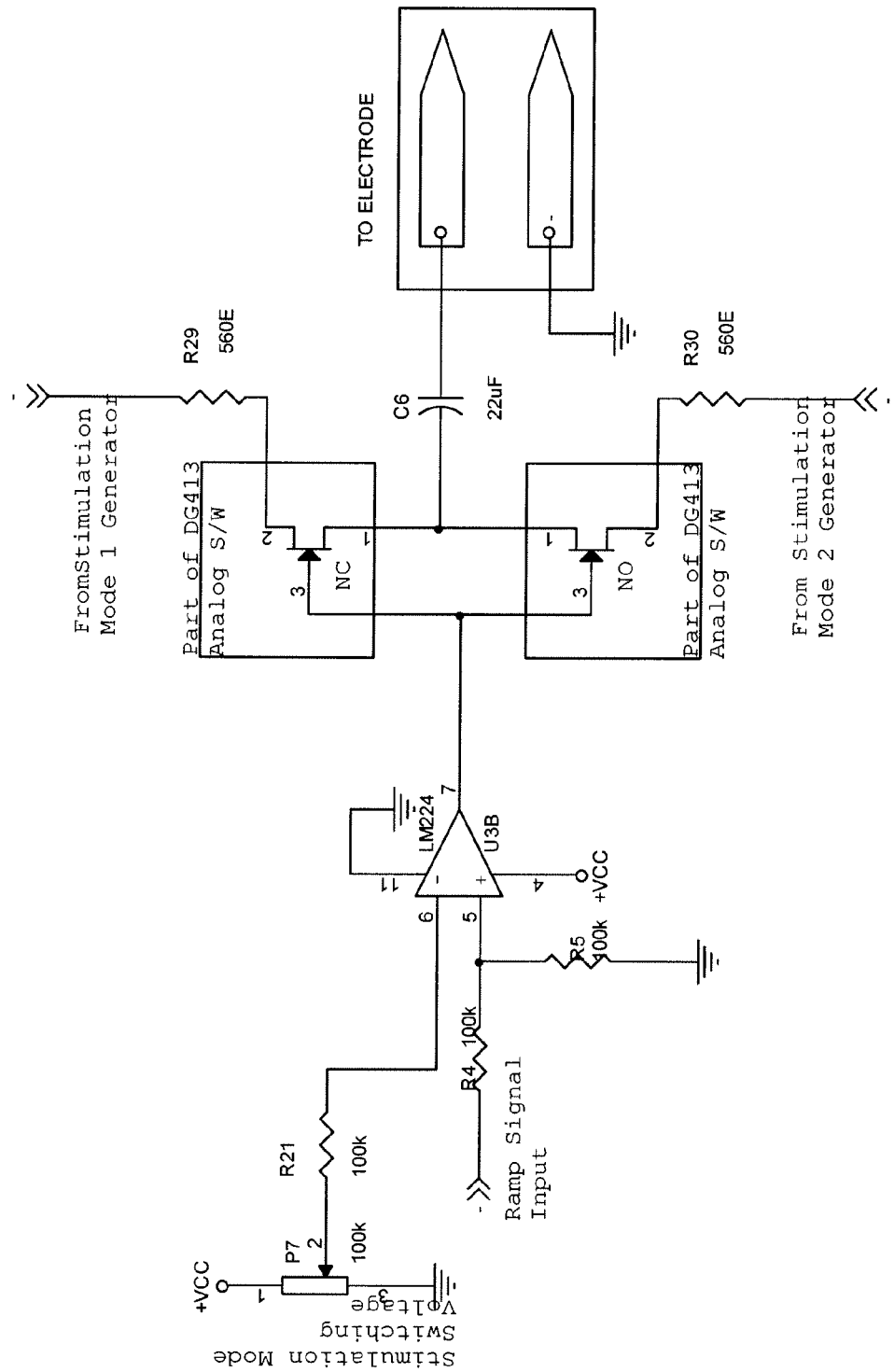
FIG. 15 depicts a stimulation mode selector circuit in accordance with an embodiment of the present invention.
Figure 16:
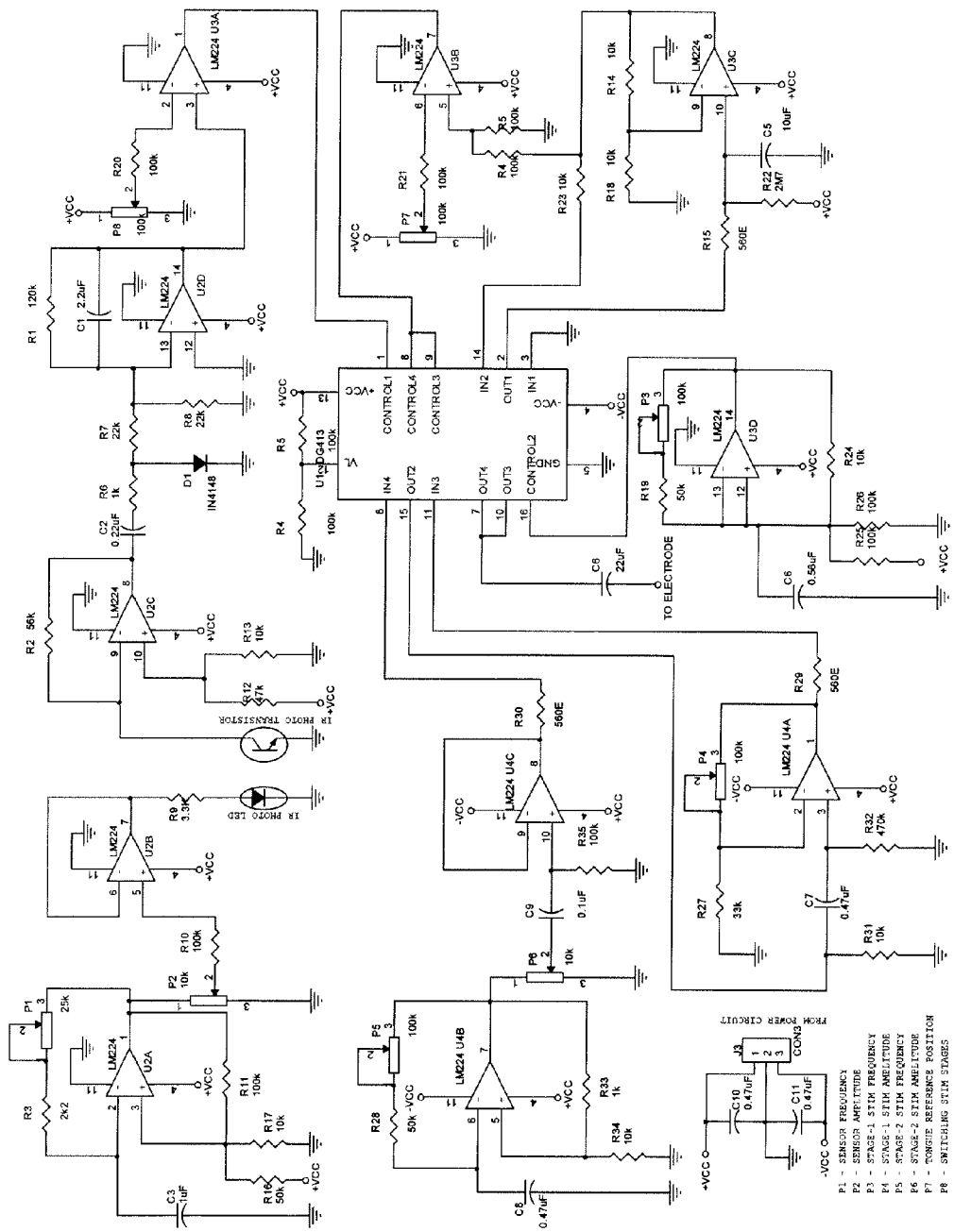
FIG. 16 depicts a control and stimulation circuit in accordance with an embodiment of the present invention.
Figure 17:
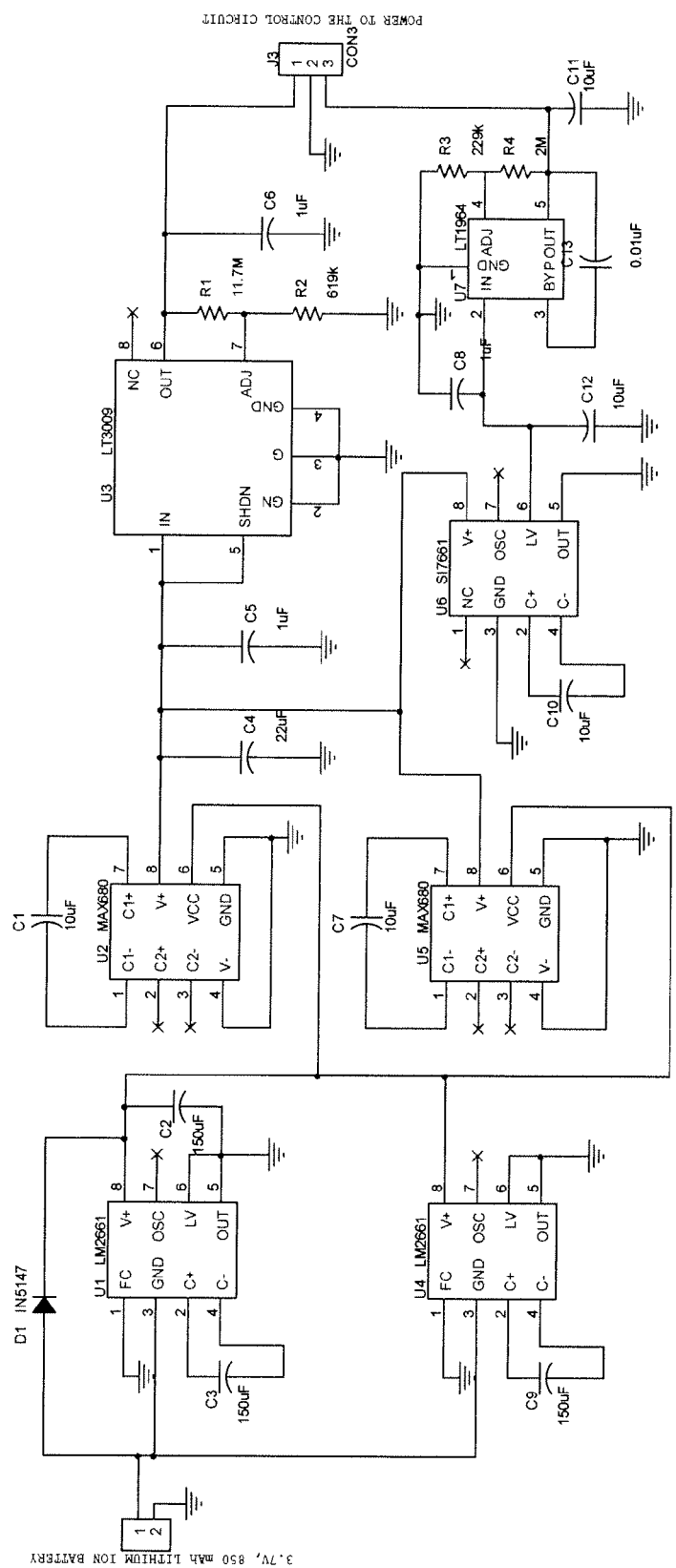
FIG. 17 depicts a power circuit in accordance with an embodiment of the present invention.

A stimulation mode selector is shown in FIG. 15. The output of comparator UB3 normally is low direct the mode 1 stimulation to the stimulating electrode on the ventral surface of the user's tongue. If the tongue does not move back into contact with the sensor or exert the prescribed amount of force against the sensor position within a prescribed amount of time after the start of the voltage ramp, the voltage ramp from the integrator will reach a level at which the output of comparator U3B goes high. The ramp voltage at which this occurs is set by potentiometer P7. This disconnects the mode 1 stimulator from the stimulating electrodes and connects the mode 2 stimulator to the electrodes.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A device for use with a patient having a mouth, a tongue, and an airway, the tongue being positionable in a portion of the mouth whereat the airway is unobstructed by the tongue, the device comprising:
　at least one sensor configured to generate a signal encoding information related to the position of the tongue in the patient's mouth;
　at least one electrical stimulus generator;
　at least one processor configured to (a) receive the signal generated by the at least one sensor, (b) determine based upon the information related to the position of the tongue in the patient's mouth encoded in the signal whether the tongue is in the portion of the mouth whereat the airway is unobstructed by the tongue, and (c) instruct the at least one electrical stimulus generator to generate electrical stimulation if the at least one processor determines the tongue is not in the portion of the mouth whereat the airway is unobstructed by the tongue; and
　at least one electrode positionable against the tongue of the patient configured to receive the electrical stimulation generated by the electrical stimulus generator, and apply the electrical stimulation to the tongue, the electrical stimulation being configured to cause the tongue to move toward the portion of the mouth whereat the airway is unobstructed by the tongue.

2. The device of claim 1, wherein the electrical stimulation applied to the tongue comprises at least one cycle of electrical pulses having amplitudes that increase over time.

3. The device of claim 2, wherein the at least one processor is further configured to instruct the at least one electrical stimulus generator to terminate generating electrical stimulation when the at least one processor determines the tongue is positioned in the portion of the mouth whereat the airway is unobstructed by the tongue.

4. A device for use with a patient having a mouth, a tongue, and an airway, the tongue being positionable in a portion of the mouth whereat the airway is unobstructed by the tongue, the device comprising:
　at least one sensor configured to generate a signal encoding information related to the position of the tongue in the patient's mouth;
　at least one electrical stimulus generator;
　at least one processor configured to (a) receive the signal generated by the at least one sensor, (b) determine based upon the information related to the position of the tongue in the patient's mouth encoded in the signal whether the tongue is in the portion of the mouth whereat the airway is unobstructed by the tongue, and (c) instruct the at least one electrical stimulus generator to generate a variable electrical stimulation signal if the at least one processor determines the tongue is not in the portion of the mouth whereat the airway is unobstructed by the tongue; and
　at least one electrode positionable against the tongue of the patient configured to receive the variable electrical stimulation signal generated by the electrical stimulus generator, and apply the variable electrical stimulation signal to the tongue, the variable electrical stimulation signal being configured to cause the tongue to move toward the portion of the mouth whereat the airway is unobstructed by the tongue.

5. The device of claim 4, wherein the variable electrical stimulation signal applied to the tongue increases over time.

6. The device of claim 5, wherein the at least one processor is further configured to instruct the at least one electrical stimulus generator to reduce the variable electrical stimulation signal when the at least one processor determines the tongue is positioned in the portion of the mouth whereat the airway is unobstructed by the tongue.

* * * * *